United States Patent
Geneste et al.

(10) Patent No.: US 9,688,678 B2
(45) Date of Patent: Jun. 27, 2017

(54) OXINDOLE COMPOUNDS CARRYING A NITROGEN-BOUND SPIRO SUBSTITUENT AND USE THEREOF FOR TREATING VASOPRESSIN-RELATED DISEASES

(71) Applicant: AbbVie Deutschland GmbH & Co. KG, Wiesbaden (DE)

(72) Inventors: Hervé Geneste, Ludwigshafen (DE); Wilfried Hornberger, Ludwigshafen (DE); Katja Jantos, Ludwigshafen (DE); Andreas Kling, Ludwigshafen (DE); Marcel Van Gaalen, Göttingen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 15 days.

(21) Appl. No.: 14/713,909

(22) Filed: May 15, 2015

(65) Prior Publication Data
US 2015/0329551 A1 Nov. 19, 2015

Related U.S. Application Data

(60) Provisional application No. 61/993,903, filed on May 15, 2014.

(51) Int. Cl.
C07D 471/10 (2006.01)
C07D 487/10 (2006.01)
C07D 295/135 (2006.01)
C07D 305/08 (2006.01)

(52) U.S. Cl.
CPC ....... *C07D 471/10* (2013.01); *C07D 295/135* (2013.01); *C07D 305/08* (2013.01); *C07D 487/10* (2013.01)

(58) Field of Classification Search
CPC C07D 295/135; C07D 305/08; C07D 471/10; C07D 487/10
USPC ......... 514/210.21, 278; 546/15; 544/70, 230
See application file for complete search history.

(56) References Cited

U.S. PATENT DOCUMENTS

2009/0318406 A1 12/2009 Geneste et al.

FOREIGN PATENT DOCUMENTS

WO 2008/025735 3/2008

OTHER PUBLICATIONS

Chan et al. "Discovery and design . . . " Exp, Physiology 85S, 7S-18S (2000).*

(Continued)

*Primary Examiner* — Celia Chang
(74) *Attorney, Agent, or Firm* — Neal, Gerber & Eisenberg LLP

(57) ABSTRACT

The present invention relates to novel substituted oxindole derivatives of the formula I

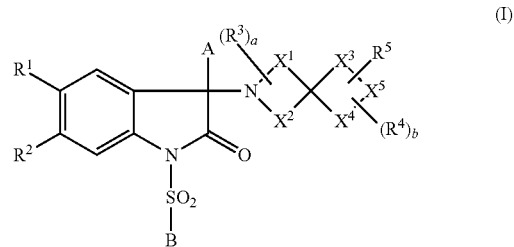

(I)

wherein A is a ring selected from phenyl and 6-membered hetaryl containing 1 or 2 nitrogen atoms as ring members, where ring A carries one substituent $R^6$ and optionally one substituent $R^7$; B is a ring selected from phenyl and a monocyclic or bicyclic heteroaromatic ring containing 1, 2 or 3 heteroatoms selected from O, N and S as ring members, where ring B may carry 1, 2 or 3 substituents $R^8$; $X^1$, $X^2$, $X^3$ and $X^4$, independently of each other, are selected from —$CH_2$—, —O—, —S(O)$_c$—, —NH—, —C(O)—, —$CH_2CH_2$—, —$CH_2O$—, —$OCH_2$—, —S(O)$_c$$CH_2$—, —$CH_2S(O)_c$—, $CH_2NH$—, —$NHCH_2$—, —$CH_2C(O)$— and C(O)$CH_2$—;

$X^5$ is NH, $CH_2$ or O; and wherein c, $R^1$, $R^2$, $(R^3)_a$, $(R^4)_b$, $R^5$, $R^6$, $R^7$, and $R^8$ are as defined in the claims.

The present invention also relates to pharmaceutical compositions comprising the novel substituted oxindole derivatives of the formula I, and to their use for the treatment of vasopressin-related disorders.

31 Claims, No Drawings

(56) References Cited

OTHER PUBLICATIONS

Fabio et al. "Vasopressin anta . . . " Frontiers in CNS drug disc. 1, 156-183 (2010).*
Hagiwara et al. "Molecular modeling . . . " Exp. Opin. Drug discov. 8(8) 951-964 (2013).*
Isotope mixture, Answers.com. p. 1 (2016).*
Deteriation unpreditable "D is for . . . " p. 28-30 (2013).*
Tung "The development of deuterium . . . " Innovations in Pharm Tech. 32, p. 1-4 (2010).*
International Search Report for Application No. PCT/EP2015/060763 dated Jul. 21, 2015 (4 pages).
Serradeil-Le Gal, C. et al., "Chracterization of SR 121463A, a highly potent-selective, orally active vasopressin V2 receptor antagonist," J. Clin. Invest. (1996) 98(12):2729-2738.

\* cited by examiner

OXINDOLE COMPOUNDS CARRYING A NITROGEN-BOUND SPIRO SUBSTITUENT AND USE THEREOF FOR TREATING VASOPRESSIN-RELATED DISEASES

CROSS-REFERENCE TO RELATED APPLICATION(S)

This claims priority to U.S. Provisional Patent Application No. 61/993,903, filed on May 15, 2014, the entire contents of which is fully incorporated herein by reference.

The present invention relates to novel substituted oxindole derivatives, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3, and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life Sci. 63 (2006), 1766-1779).

1-(Het)Arylsulfonyl-1,3-dihydro-2H-indol-2-ones have previously been described as ligands of vasopressin receptors, for example in WO 2005/030755, WO 2006/005609, WO 2006/080574, WO 2008/080970, WO 2008/080971, WO 2008/080972, WO 2008/080973, WO 2009/071687, WO 2009/071689, WO 2009/071690, WO2009/071691, WO 2009/083559, WO 2010/009775 or WO 2010/142739.

WO 2008/025735 describes substituted oxindole compounds which have a monocyclic or fused bicyclic substituent linked via a nitrogen atom in position 3.

WO 2008/107399 describes substituted oxindole compounds which have a 5- or 6-membered saturated, unsaturated or aromatic heterocyclic radical linked via a bivalent functional group to the oxindole structure in position 3. The bivalent group comprises a nitrogen atom and may comprise a saturated carbocycle or heterocycle and is attached via the nitrogen atom to the oxindole structure.

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity;

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/ml);

7.) suitable pharmacokinetics (time course of the concentration of the compound of the invention in plasma or in tissue, for example brain). The pharmacokinetics can be described by the following parameters: half-life (in h), volume of distribution (in l·kg-1), plasma clearance (in l·h−1·kg-1), AUC (area under the curve, area under the concentration-time curve, in ng·h·l−1), oral bioavailability (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-related diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I

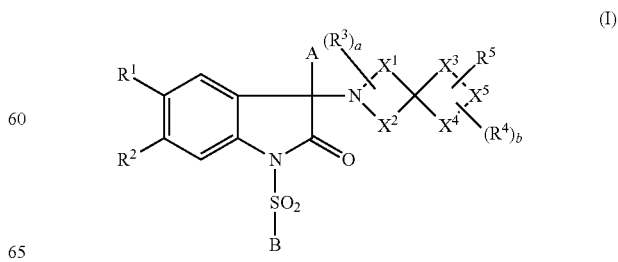

wherein

A is a ring selected from phenyl and 6-membered hetaryl containing 1 or 2 nitrogen atoms as ring members, where ring A carries one substituent $R^6$ and optionally one substituent $R^2$;

B is a ring selected from phenyl and a monocyclic or bicyclic heteroaromatic ring containing 1, 2 or 3 heteroatoms selected from O, N and S as ring members, where ring B may carry 1, 2 or 3 substituents $R^8$;

$X^1$, $X^2$, $X^3$ and $X^4$, independently of each other, are selected from —$CH_2$—, —O—, —$S(O)_c$—, —NH—, —C(O)—, —$CH_2CH_2$—, —$CH_2O$—, —$OCH_2$—, —$S(O)_cCH_2$—, —$CH_2S(O)_c$—, $CH_2NH$—, —$NHCH_2$—, —$CH_2C(O)$— and —$C(O)CH_2$—;

$X^5$ is NH, $CH_2$ or 0;

$R^1$ is selected from hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^2$ is selected from hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^3$ and $R^4$, independently of each other and independently of each occurrence, are selected from hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy and $NR^9R^{10}$, and in case that $R^3$ or $R^4$ are bound to a carbon ring atom, are additionally selected from halogen; or two non-geminal radicals $R^3$ form together a group —$(CH_2)_k$—, where k is 1, 2, 3 or 4, where 1 or 2 hydrogen atoms in this group may be replaced by a methyl group; or two non-geminal radicals $R^4$ form together a group —$(CH_2)_k$—, where k is 1, 2, 3 or 4, where 1 or 2 hydrogen atoms in this group may be replaced by a methyl group; or two geminal radicals $R^3$ form together a group —$(CH_2)_j$—, where j is 2, 3, 4 or 5, where 1 or 2 hydrogen atoms in this group may be replaced by a methyl group; or two geminal radicals $R^4$ form together a group —$(CH_2)_j$—, where j is 2, 3, 4 or 5, where 1 or 2 hydrogen atoms in this group may be replaced by a methyl group;

with the proviso that $R^3$ and $R^4$ are not halogen, hydroxyl, $C_1$-$C_4$-alkoxy or $C_1$-$C_4$-haloalkoxy if they are bound to a carbon atom in α-position to a nitrogen ring atom;

$R^5$ is selected from hydrogen, cyano, $C_1$-$C_6$-alkyl, $C_2$-$C_6$-alkenyl, $C_2$-$C_6$-alkynyl, $C_3$-$C_7$-cycloalkyl, where the four last-mentioned radicals may be partially or fully halogenated and/or may carry one or more substituents $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; —$OR^{13}$; —$S(O)_lR^{13}$; $NR^{14}R^{15}$; and —C(=O)$R^{16}$;

$R^6$ and $R^7$, independently of each other, are selected from halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

each $R^8$ is independently selected from halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^9$ and $R^{10}$, independently of each other, are selected from hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl;

each $R^{11}$ is independently selected from cyano, —$OR^{13}$, —$S(O)_lR^{13}$, $NR^{14}R^{15}$, —C(=O)$R^{16}$, $C_3$-$C_6$-cycloalkyl, $C_3$-$C_6$-halocycloalkyl, phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members, and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally selected from $C_1$-$C_4$-alkyl and $C_1$-$C_4$-haloalkyl;

each $R^{12}$ is independently selected from halogen, hydroxyl, cyano, nitro, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenyl, phenoxy, benzyloxy, where the phenyl moiety in the three last-mentioned radicals may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members, where the heteromonocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{13}$ is independently selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl which may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

$R^{14}$ and $R^{15}$, independently of each other and independently of each occurrence, are selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl which may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; $C_1$-$C_4$-alkylcarbonyl and $C_1$-$C_4$-haloalkylcarbonyl;

each $R^{16}$ is independently selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl, —$OR^{13}$ and $NR^{14}R^{15}$;

a is 0, 1 or 2;
b is 0, 1 or 2;
c is 0, 1 or 2; and
l is 0, 1 or 2;

and the N-oxides, stereoisomers and pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhäuser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

The term "stereoisomers" encompasses both optical isomers, such as enantiomers or diastereomers, the latter existing due to more than one center of chirality in the molecule, as well as geometrical isomers (cis/trans isomers; correctly speaking, these are also diastereomers). The term "stereoisomers" also encompasses conformers (to be more precise configuration isomers) which are caused by the hindered or decelerated inversion at one or more nitrogen atoms, especially ring nitrogen atoms, such as $X^5$ (if this is N, of course); like the isomers described by Y. Naruse et al. in Tetrahedron Asymmetry 2013, 24, 169-171.

Depending on the substitution pattern, the compounds of the formula I may have one or more centers of chirality, in which case they are present as mixtures of enantiomers or diastereomers. One center of chirality is the carbon ring atom in the 3-position of the oxindole scaffold (the carbon atom which carries the group A and the N-bound spiro rings). The compounds of the formula I may further have axial chirality due to the spiro system. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

Halogen in the terms of the present invention is fluorine, chlorine, bromine or iodine, preferably fluorine, chlorine or bromine and especially fluorine or chlorine.

$C_1$-$C_3$-Alkyl is a linear or branched alkyl radical having 1 to 3 carbon atoms, such as methyl, ethyl, n-propyl or isopropyl. $C_1$-$C_4$-Alkyl is a linear or branched alkyl radical having 1 to 4 carbon atoms, such as methyl, ethyl, n-propyl, isopropyl, n-butyl, sec-butyl, isobutyl or tert-butyl. $C_1$-$C_6$-Alkyl is a linear or branched alkyl radical having 1 to 6 carbon atoms, such as methyl, ethyl, n-propyl, isopropyl, n-butyl, sec-butyl, isobutyl, tert-butyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

Fluorinated alkyl is a straight-chain or branched alkyl group having from 1 to 4 (=fluorinated $C_1$-$C_4$-alkyl), in particular 1 to 3 carbon atoms (=fluorinated $C_1$-$C_3$-alkyl), more preferably 1 or 2 carbon atoms (=fluorinated $C_1$-$C_2$-alkyl), wherein at least one, e.g. 1, 2, 3, 4 or all of the hydrogen atoms are replaced by fluorine atoms. Examples for fluorinated $C_1$-$C_2$-alkyl are fluorinated methyl such as fluoromethyl, difluoromethyl, trifluoromethyl, and fluorinated ethyl such as 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, pentafluoroethyl and the like. Examples for fluorinated $C_1$-$C_3$-alkyl are, apart those mentioned above for fluorinated $C_1$-$C_2$-alkyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl and the like. Examples for fluorinated $C_1$-$C_4$-alkyl are, apart those mentioned above for fluorinated $C_1$-$C_3$-alkyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

Haloalkyl, which is also expressed as "alkyl which is partially or fully halogenated", is a straight-chain or branched alkyl group having from 1 to 6 (=$C_1$-$C_6$-haloalkyl), in particular 1 to 4 carbon atoms (=$C_1$-$C_4$-haloalkyl), wherein at least one, e.g. 1, 2, 3, 4 or all of the hydrogen atoms are replaced by a halogen atom. Examples for $C_1$-$C_4$-haloalkyl are, apart those mentioned above for fluorinated $C_1$-$C_4$-alkyl, chloromethyl, bromomethyl, dichloromethyl, trichloromethyl, chlorofluoromethyl, dichlorofluoromethyl, chlorodifluoromethyl, 1-chloroethyl, 1-bromoethyl, 2-chloro-2-fluoroethyl, 2-chloro-2,2-difluoroethyl, 2,2-dichloro-2-fluoroethyl, 2,2,2-trichloroethyl, 3-chloropropyl, 4-chlorobutyl and the like. Examples for $C_1$-$C_6$-haloalkyl are, apart from those listed for $C_1$-$C_4$-haloalkyl, 1-fluoropentyl, 1-chloropenthyl, 1-bromopentyl, 1-fluorohexyl, 1-chlorohexy, 1-bromohexyl and the like.

$C_1$-$C_3$-Hydroxyalkyl is $C_1$-$C_3$-alkyl as defined above wherein one of the hydrogen atoms is replaced by a hydroxyl group. Examples are hydroxymethyl, 1- and 2-hydroxyethyl, 1-, 2- and 3-hydroxy-n-propyl, 1-(hydroxymethyl)-ethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position. Examples for $C_2$-$C_3$-alkenyl are ethenyl, 1-propenyl, 2-propenyl or 1-methylethenyl. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl. Examples for $C_2$-$C_6$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position. Examples for $C_2$-$C_3$-alkynyl are ethynyl, 1-propynyl or 2-propynyl. Examples for $C_2$-$C_4$-alkynyl are ethynyl, 1-propynyl, 2-propynyl, 1-butynyl, 2-butynyl, 3-butynyl, 1-methyl-2-propynyl and the like. Examples for $C_2$-$C_6$-alkynyl are ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl") or 2 to 6 ("$C_2$-$C_6$-haloalkynyl") carbon atoms and one or two triple bonds in any position (as mentioned above), where some or all of the hydrogen atoms in these groups are replaced by halogen atoms as mentioned above, in particular fluorine, chlorine and bromine.

$C_3$-$C_7$-Cycloalkyl is a monocyclic saturated hydrocarbon radical having 3 to 7, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkyl comprise cyclopropyl and cyclobutyl. Examples of $C_3$-$C_5$-cycloalkyl comprise cyclopropyl, cyclobutyl and cyclopentyl. Examples of $C_3$-$C_6$-cycloalkyl comprise cyclopropyl, cyclobutyl, cyclopentyl and cyclohexyl. Examples of $C_3$-$C_7$-cycloalkyl comprise cyclopropyl, cyclobutyl, cyclopentyl, cyclohexyl and cycloheptyl.

Fluorinated $C_3$-$C_7$-cycloalkyl is a monocyclic saturated hydrocarbon radical having 3 to 7, in particular 3 to 6 ("fluorinated $C_3$-$C_6$-cycloalkyl") or 3 to 5 ("fluorinated $C_3$-$C_5$-cycloalkyl") or 3 to 4 ("fluorinated $C_3$-$C_4$-cycloalkyl") carbon ring members (as mentioned above) in which some or all of the hydrogen atoms are replaced by fluorine atoms. Examples for fluorinated $C_3$-$C_4$-cycloalkyl are 1-fluorocyclopropyl, 2-fluorocyclopropyl, 2,2-difluorocyclopropyl, 1-fluorocyclobutyl, 2-fluorocyclobutyl, 3-fluorocyclobutyl, 2,2-difluorocyclobutyl, 3,3-difluorocyclobutyl and the like. Examples for fluorinated $C_3$-$C_5$-cycloalkyl are additionally 1-fluorocyclopentyl, 2-fluorocyclopentyl, 3-fluorocyclopentyl, 2,2-difluorocyclopentyl, 3,3-difluorocyclopentyl, and the like. Examples for fluorinated $C_3$-$C_6$-cycloalkyl are additionally 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, and the like. Examples for fluorinated $C_3$-$C_7$-cycloalkyl are additionally 1-fluorocycloheptyl, 2-fluorocycloheptyl, 3-fluorocycloheptyl, 4-fluorocycloheptyl, 2,2-difluorocycloheptyl, 3,3-difluorocycloheptyl, 4,4-difluorocycloheptyl, and the like $C_3$-$C_7$-Halocycloalkyl is a monocyclic saturated hydrocarbon radical having 3 to 7, in particular 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "$C_3$-$C_6$-cycloalkyl-$C_1$-$C_4$-alkyl" which is bound to the remainder of the molecule via a $C_1$-$C_4$-alkyl group, as defined above. Examples for $C_3$-$C_6$-cycloalkyl-$C_1$-$C_4$-alkyl are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl and cyclohexylpropyl.

$C_3$-$C_6$-Cycloalkylmethyl is for example cyclopropylmethyl, cyclobutylmethyl, cyclopentylmethyl and cyclohexylmethyl.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy.

$C_1$-$C_4$-Haloalkoxy is $C_1$-$C_4$-alkoxy as defined above wherein at least one, e.g. 1, 2, 3, 4 or all of the hydrogen atoms are replaced by a halogen atom. Preferably, $C_1$-$C_4$-haloalkoxy is fluorinated $C_1$-$C_4$-alkoxy. This is a straight-chain or branched alkoxy group having from 1 to 4, in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.

The term "$C_1$-$C_4$-alkoxy-$C_1$-$C_2$-alkyl" as used herein, refers to a straight-chain or branched alkyl group having 1 to 2 carbon atoms, as defined above, where one hydrogen atom is replaced by a $C_1$-$C_4$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tertbutoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "fluorinated $C_1$-$C_4$-alkoxy-$C_1$-$C_2$-alkyl" as used herein, refers to a straight-chain or branched alkyl group having 1 to 2 carbon atoms, as defined above, where one hydrogen atom is replaced by a $C_1$-$C_4$-alkoxy group, as defined above, and wherein at least one, e.g. 1, 2, 3, 4 or all of the remaining hydrogen atoms (either in the alkoxy moiety or in the alkyl moiety or in both) are replaced by fluorine atoms. The term "fluorinated $C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above, and wherein at least one, e.g. 1, 2, 3, 4 or all of the remaining hydrogen atoms (either in the alkoxy moiety or in the alkyl moiety or in both) are replaced by fluorine atoms. The term "fluorinated $C_1$-$C_6$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_6$-alkoxy group, as defined above, and wherein at least one, e.g. 1, 2, 3, 4 or all of the remaining hydrogen atoms (either in the alkoxy moiety or in the alkyl moiety or in both) are replaced by fluorine atoms. Examples are difluoromethoxymethyl ($CHF_2OCH_2$), trifluoromethoxymethyl ($CF_3OCH_2$), 1-difluoromethoxyethyl ($CHF_2OCH(CH_3)$), 1-trifluoromethoxyethyl ($CF_3OCH(CH_3)$), 2-difluoromethoxyethyl ($CHF_2OCH_2CH_2$), 2-trifluoromethoxyethyl ($CF_3OCH_2CH_2$), methoxy-difluoromethyl ($CH_3OCF_2$), 2-methoxy-1,1-difluoroethyl ($CH_3OCH_2CF_2$), 2-methoxy-2,2-difluoroethyl ($CH_3OCF_2CH_2$), and the like.

$C_1$-$C_4$-Alkylthio is a $C_1$-$C_4$-alkyl group, as defined above, attached via a sulfur atom. Examples are methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

$C_1$-$C_4$-Haloalkylthio is a $C_1$-$C_4$-haloalkyl group, as defined above, attached via a sulfur atom. Examples are $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio.

$C_1$-$C_4$-Alkylsulfinyl is a $C_1$-$C_4$-alkyl group, as defined above, attached via a sulfinyl [S(O)] group. Examples are methylsulfinyl, ethylsulfinyl, n-propylsulfinyl, 1-methylethylsulfinyl (isopropylsulfinyl), butylsulfinyl, 1-methylpropylsulfinyl (secbutylsulfinyl), 2-methylpropylsulfinyl (isobutylsulfinyl) or 1,1-dimethylethylsulfinyl (tert-butylsulfinyl).

$C_1$-$C_4$-Haloalkylsulfinyl is a $C_1$-$C_4$-haloalkyl group, as defined above, attached via a sulfinyl [S(O)] group. Examples are $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, S(O)C$_2$F$_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, S(O)CH$_2$—C$_2$F$_5$, S(O)CF$_2$—C$_2$F$_5$, 1-(CH$_2$F)-2-fluoroethylsulfinyl, 1-(CH$_2$Cl)-2-chloroethylsulfinyl, 1-(CH$_2$Br)-2-bromoethylsulfinyl, 4-fluorobutylsulfinyl, 4-chlorobutylsulfinyl, 4-bromobutylsulfinyl or nonafluorobutylsulfinyl.

C$_1$-C$_4$-Alkylsulfonyl is a C$_1$-C$_4$-alkyl group, as defined above, attached via a sulfonyl [S(O)$_2$] group. Examples are methylsulfonyl, ethylsulfonyl, n-propylsulfonyl, 1-methylethylsulfonyl (isopropylsulfonyl), butylsulfonyl, 1-methylpropylsulfonyl (secbutylsulfonyl), 2-methylpropylsulfonyl (isobutylsulfonyl) or 1,1-dimethylethylsulfonyl (tert-butylsulfonyl).

C$_1$-C$_4$-Haloalkylsulfonyl is a C$_1$-C$_4$-haloalkyl group, as defined above, attached via a sulfonyl [S(O)$_2$] group. Examples are S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, S(O)$_2$C$_2$F$_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl, 1-(CH$_2$Br)-2-bromoethylsulfonyl, 4-fluorobutylsulfonyl, 4-chlorobutylsulfonyl, 4-bromobutylsulfonyl or nonafluorobutylsulfonyl.

C$_1$-C$_4$-Alkylcarbonyl is a C$_1$-C$_4$-alkyl group, as defined above, attached via a carbonyl [C(═O)] group. Examples are acetyl (methylcarbonyl), propionyl (ethylcarbonyl), propylcarbonyl, isopropylcarbonyl, n-butylcarbonyl and the like.

C$_1$-C$_4$-Haloalkylcarbonyl is a C$_1$-C$_4$-haloalkyl group, as defined above, attached via a carbonyl [C(═O)] group. Examples are trifluoromethylcarbonyl, 2,2,2-trifluoroethylcarbonyl and the like.

Examples for "6-membered hetaryl containing 1 or 2 nitrogen atoms as ring members" are pyridyl, such as pyridin-2-yl, pyridin-3-yl or pyridin-4-yl, pyridazinyl, such as pyridazin-3-yl or pyridazin-4-yl, pyrimidinyl, such as pyrimidin-2-yl, pyrimidin-4-yl or pyrimidin-5-yl, and pyrazinyl.

The term "3-, 4-, 5-, 6- or 7-membered saturated, partially unsaturated or maximally unsaturated heterocyclic ring containing 1, 2 or 3 heteroatoms or heteroatom groups selected from O, N, S, NO, SO and SO$_2$ as ring members" denotes a 3-, 4-, 5-, 6- or 7-membered saturated, partially unsaturated or maximum unsaturated heteromonocyclic ring containing 1, 2 or 3 heteroatoms or heteroatom groups selected from O, N, S, NO, SO and SO$_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. Partially unsaturated rings contain less C—C and/or C—N and/or N—N double bonds than allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 heteroatoms or heteroatom groups selected from O, N, S, NO, SO and SO$_2$, as ring members" [wherein "maximum unsaturated" includes also "aromatic"] as used herein denotes monocyclic radicals, the monocyclic radicals being saturated, partially unsaturated or maximum unsaturated (including aromatic). 7-membered rings cannot be aromatic; they are homoaromatic if maximally unsaturated (3 double bonds).

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3- dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples for a bicyclic heteroaromatic ring containing 1, 2 or 3 heteroatoms selected from O, S and N as ring members are bicyclic 8-, 9- or 10-membered hetaryl. Preferably, bicyclic hetaryl has one of the aforementioned 5- or 6-membered heteroaromatic rings and a further aromatic carbocycle or 5- or 6-membered aromatic heterocycle fused thereto, for example a fused benzene, thiophene, furane, pyrrole, pyrazole, imidazole, pyridine or pyrimidine ring. These bicyclic hetaryl include for example 9-membered hetaryl such as indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl and 10-membered hetaryl such as quinolinyl, isoquinolinyl, cinnolinyl, naphthyridin-5-yl, naphthyridin-6-yl, naphthyridin-7-yl and naphthyridin-8-yl.

The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals A, B, $X^1$, $X^2$, $X^3$, $X^4$, $X^5$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, a, b, c and 1 in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

As a matter of course, each radical $R^3$, if present, replaces a hydrogen atom of the ring members $X^1$ and/or $X^2$, e.g. the hydrogen(s) atom in the $CH_2$ or NH moieties of $X^1$ and/or $X^2$.

Alike, each radical $R^4$, if present, replaces a hydrogen atom of the ring members $X^3$, $X^4$ and/or $X^5$, e.g. the hydrogen atom(s) in the $CH_2$ or NH moieties of $X^3$, $X^4$ and/or X.

$R^5$ can be bound to any of the ring members $X^3$, $X^4$ and/or $X^5$, but if $X^5$ is NH or $CH_2$, $R^5$ is preferably bound to $X^5$, where it replaces a hydrogen atom of this NH or $CH_2$ group $X^5$ (so that $X^5$ is $NR^5$ or $CHR^5$ or $C(R^4)R^5$).

If $X^1$, $X^2$, $X^3$, $X^4$ or $X^5$ are NH, preferably they do not carry an N-bound radical $R^3$, $R^4$ or $R^5$.

In a preferred embodiment $X^1$, $X^2$, $X^3$ and $X^4$, independently of each other, are selected from —$CH_2$— and —$CH_2CH_2$—. In particular, $X^1$, $X^2$, $X^3$ and $X^4$ are —$CH_2$—.

In a further preferred embodiment, $X^5$ is NH or $CH_2$, and in particular NH.

In a further preferred embodiment, $R^5$ is bound to $X^5$, so that $X^5$ is $NR^5$ or $CHR^5$ or $C(R^4)R^5$).

A is preferably phenyl or pyridyl, in particular phenyl or 3-pyridyl, where A carries one substituent $R^6$ and optionally one substituent $R^7$.

In a preferred embodiment, A is phenyl or 3-pyridyl, where A carries the radical $R^6$ in the 2-position and the radical $R^7$, if present, in the 4- or 5-position, relative to the 1-position of the attachment point of A to the remainder of the molecule.

In particular, A is phenyl or 3-pyridyl, and carries the radical $R^6$ in the 2-position, relative to the 1-position of the attachment point of A to the remainder of the molecule, and carries the radical $R^7$ (if present) in the 5-position, relative to the 1-position of the attachment point of A to the remainder of the molecule.

B is a ring selected from phenyl and a monocyclic or bicyclic heteroaromatic ring containing 1, 2 or 3 heteroatoms selected from O, N and S as ring members, where ring B may carry 1, 2 or 3 substituents $R^8$. The monocyclic or bicyclic heteroaromatic ring is usually selected from a 5- or 6-membered monocyclic heteroaromatic ring and an aromatic 8-, 9- or 10-membered fused heterobicyclic ring system, the ring or the ring system containing 1, 2 or 3 heteroatoms selected from O, N and S as ring members and the ring or the ring system being unsubstituted or substituted 1, 2 or 3 identical or different substituents $R^8$.

B is preferably selected from phenyl, pyridyl and a 10-membered bicyclic heteroaromatic ring containing 1 or 2 nitrogen atoms as ring members, where B may carry 1, 2 or 3 identical or different substituents $R^8$. More preferably, B is selected from phenyl, pyridyl and quinolinyl, and in particular from phenyl, 2-pyridyl, 3-pyridyl and quinolin-8-yl, where B may carry 1, 2 or 3 substituents $R^8$.

In case that B is quinolin-8-yl, the quinolinyl ring is preferably unsubstituted or carries 1 substituent $R^8$, where the substituent $R^8$ is bound in the 4- or 5-position, relative to the 1-position of the attachment point of B to the remainder of the molecule (i.e. to the sulfonyl group).

In case that B is 2-pyridyl and carries one substituent $R^8$, $R^8$ is preferably bound in the 3- or 4-position, relative to the 1-position of the attachment point of B to the remainder of the molecule (i.e. to the sulfonyl group).

In case that B is 3-pyridyl and carries one substituent $R^8$, $R^8$ is preferably bound in the 4-position, relative to the 1-position of the attachment point of B to the remainder of the molecule (i.e. to the sulfonyl group).

In case that B is phenyl and carries one substituent $R^8$, this is preferably bound in the 2- or 4-position, relative to the 1-position of the attachment point of B to the remainder of the molecule (i.e. to the sulfonyl group).

In case that B is 2-pyridyl and carries two substituents $R^8$, these are preferably bound in the 4- and 5- or 4- and 6-positions, relative to the 1-position of the attachment point of B to the remainder of the molecule (i.e. to the sulfonyl group).

In case that B is phenyl and carries two substituents $R^8$, these are preferably bound in the 2- and 4-positions, relative to the 1-position of the attachment point of B to the remainder of the molecule (i.e. to the sulfonyl group).

In case that B is phenyl and carries three substituents $R^8$, these are preferably bound in the 2-, 4- and 6-positions, relative to the 1-position of the attachment point of B to the remainder of the molecule (i.e. to the sulfonyl group).

$R^1$ is preferably selected from hydrogen, halogen and cyano. More preferably, $R^1$ is selected from hydrogen, chlorine and cyano. Particularly, $R^1$ is selected from hydrogen and cyano. Specifically, $R^1$ is cyano.

$R^2$ is preferably selected from hydrogen, halogen and cyano. More preferably, $R^2$ is selected from hydrogen, fluorine and cyano. Particularly, $R^2$ is selected from hydrogen and cyano. Specifically, $R^2$ is hydrogen.

$R^3$ and $R^4$, independently of each other and independently of each occurrence, are preferably selected from halogen and $C_1$-$C_4$-alkyl, preferably from F, Cl and $CH_3$, with the proviso that $R^3$ and $R^4$ are not halogen if they are bound to a carbon atom in α-position to a nitrogen ring atom and are in particular $CH_3$.

$R^5$ is preferably selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkyl which carries one substituent $R^{11}$; phenyl which may carry 1, 2 or 3 identical or different substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 identical or different substituents $R^{12}$.

More preferably, $R^5$ is selected from $C_1$-$C_6$-alkyl which carries one substituent $R^{11}$; a 3-, 4-, 5- or 6-membered saturated heteromonocyclic ring containing 1 or 2 heteroatoms or heteroatom groups selected from O, N, S, NO, SO and $SO_2$ as ring members; and a 5- or 6-membered heteroaromatic ring containing 1 or 2 heteroatoms selected from O, N and S as ring members, where the saturated heteromonocyclic or the heteroaromatic ring may carry 1, 2 or 3 substituents $R^{12}$.

The 4-, 5- or 6-membered saturated heteromonocyclic ring $R^5$ containing 1 or 2 heteroatoms selected from O, N and S as ring members is in particular selected from oxetan-3-yl, azetidin-3-yl, pyrrolidin-3-yl, piperidin-4-yl, piperazin-1-yl and morpholin-4-yl, in particular from piperidin-4-yl, piperazin-1-yl and morpholin-4-yl, where the 4-, 5- or 6-membered saturated heteromonocyclic ring $R^5$ is unsubstituted or carries 1 or 2 substituent $R^{12}$.

The 5- or 6-membered heteroaromatic ring containing 1 or 2 heteroatoms selected from O, N and S as ring members is in particular selected from pyrrolyl, imidazolyl, pyridyl and pyrimidinyl, in particular from pyridine-2-yl, pyridine-3-yl and pyridine-4-yl, and is specifically pyridine-4-yl, where the 5- or 6-membered heteroaromatic ring is unsubstituted or carries 1 or 2 substituent $R^{12}$.

In particular, $R^5$ is selected from $C_1$-$C_4$-alkyl which carries one substituent $R^{11}$; a 6-membered saturated heteromonocyclic ring containing 1 or 2 heteroatoms selected from O and N as ring members; and a 6-membered heteroaromatic ring containing 1 or 2 nitrogen atoms as ring members, where the saturated heteromonocyclic or the heteroaromatic ring may carry 1 or 2 substituents $R^{12}$.

$R^{11}$ is preferably selected from cyano; —$OR^{13}$; $NR^{14}R^{15}$; a 3-, 4-, 5-, 6- or 7-membered saturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated heterobicyclic ring containing 1, 2 or 3 heteroatoms or heteroatom groups selected from O, N, S, NO, SO and $SO_2$ as ring members, where the heteromoncyclic or heterobicyclic ring may carry 1, 2 or 3 substituents $R^{12}$; and as a substituent on a cycloalkyl ring, $R^{11}$ is additionally selected from $C_1$-$C_4$-alkyl and $C_1$-$C_4$-haloalkyl.

More preferably, $R^{11}$ is selected from 4-, 5- or 6-membered, in particular a 6-membered, saturated heteromonocyclic ring containing 1 or 2 heteroatoms or heteroatom groups selected from O, N, S, NO, SO and $SO_2$ as ring members, where the heteromoncyclic ring may carry 1 or 2 or 3 substituents $R^{12}$. The 6-membered saturated heteromonocyclic ring containing 1 or 2 heteroatoms or heteroatom groups selected from O, N, S, NO, SO and $SO_2$ as ring members is specifically morpholin-4-yl.

Preferably, $R^{12}$ is selected from halogen, cyano, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkyl, fluorinated $C_1$-$C_4$-alkoxy-$C_1$-$C_4$-alkyl, phenyl which may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy; and a 3-, 4-, 5- or 6-membered saturated heteromonocyclic ring containing 1, 2 or 3 heteroatoms or heteroatom groups selected from O, N, S, NO, SO and $SO_2$ as ring members, where the heteromonocyclic ring may carry 1, 2 or 3 identical or different substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy.

More preferably, $R^{12}$ is selected from $C_1$-$C_4$-alkyl, fluorinated $C_1$-$C_4$-alkyl, $C_1$-$C_4$-alkoxy-$C_1$-$C_4$-alkyl, fluorinated $C_1$-$C_4$-alkoxy-$C_1$-$C_4$-alkyl, and a 3-, 4-, 5- or 6-membered saturated heteromonocyclic ring containing 1 or 2 heteroatoms selected from O, N and S as ring members. In particular, $R^{12}$ is selected from $C_1$-$C_4$-alkyl, $C_1$-$C_4$-alkoxy-$C_1$-$C_2$-alkyl and a 4-membered saturated heteromonocyclic ring containing 1 heteroatom selected from O, S and N as ring member. Specifically, $R^{12}$ is selected from methyl, ethyl, n-propyl, isopropyl, methoxyethyl, ethoxyethyl and oxetan-3-yl.

$R^{13}$ is preferably selected from hydrogen, $C_1$-$C_4$-alkyl and $C_1$-$C_4$-haloalkyl.

$R^{14}$ and $R^{15}$ are preferably independently selected from hydrogen and $C_1$-$C_4$-alkyl.

$R^{16}$ is preferably selected from hydrogen and $C_1$-$C_4$-alkyl.

$R^6$ is preferably selected from $C_1$-$C_3$-alkoxy, $C_1$-$C_3$-alkyl and fluorinated $C_1$-$C_3$-alkyl, and in particular from methoxy, ethoxy and fluorinated ethyl.

$R^7$ is preferably selected from halogen and $C_1$-$C_3$-alkoxy, and in particular from fluorine or methoxy.

Preferably, each $R^8$ is independently selected from halogen, cyano, $C_1$-$C_3$-alkyl, fluorinated $C_1$-$C_3$-alkyl, $C_1$-$C_3$-alkoxy and fluorinated $C_1$-$C_3$-alkoxy. Especially, each $R^8$ is independently selected from fluorine, chlorine, cyano, methyl, methoxy and trifluoromethoxy and in particular from fluorine, chlorine, cyano, methyl and methoxy.

Preferably, a is 0 or 1, in particular 0.
Preferably, b is 0 or 1, in particular 0.
Specifically, a and b are each 0.

In a particular embodiment, the compound of formula I is a compound of formula IA

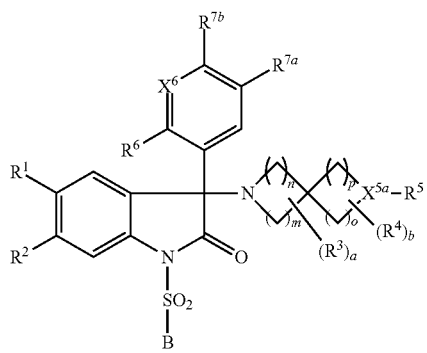

(IA)

where
B, $R^1$, $R^2$, $R^3$, $R^4$, $R^5$, $R^6$, a and b are as defined above, and have in particular one of the above preferred definitions;
$X^{5a}$ is N or CH;
$X^6$ is N or CH;
$R^{7a}$ and $R^{7b}$, independently of each other, are hydrogen or have one of the general or, in particular, one of the preferred definitions given above for $R^7$, with the proviso that at least one of $R^{7a}$ and $R^{7b}$ is hydrogen;
m, n, o and p are independently of each other 1 or 2.
Preferably, m and n are both 1 or are both 2.
Preferably, o and p are both 1 or are both 2.
Specifically, m, n, o and p are each 1.

The invention preferably relates to compounds of the formula IA in which
$X^{5a}$ is N or CH;
$X^6$ is N or CH;
B is selected from phenyl, pyridyl and a 10-membered bicyclic heteroaromatic ring containing 1 or 2 nitrogen atoms as ring members, where B may carry 1, 2 or 3 substituents $R^8$;
$R^1$ is hydrogen, halogen or cyano; in particular cyano;
$R^2$ is hydrogen, halogen or cyano; in particular hydrogen;
$R^3$ and $R^4$ independently of each other and independently of each occurrence, are selected from halogen and $C_1$-$C_4$-alkyl, with the proviso that $R^3$ and $R^4$ are not halogen if they are bound to a carbon atom in α-position to a nitrogen ring atom; and are in particular $CH_3$;
$R^5$ is selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkyl which carries one substituent $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and in case that $X^5a$ is CH, $R^5$ is additionally selected from —$OR^{13}$;
$R^6$ is $C_1$-$C_3$-alkoxy, $C_1$-$C_3$-alkyl or fluorinated $C_1$-$C_3$-alkyl;
$R^{7a}$ and $R^{7b}$, independently of each other, are hydrogen, halogen or $C_1$-$C_3$-alkoxy;
each $R^8$ is selected from halogen, cyano, $C_1$-$C_3$-alkyl, fluorinated $C_1$-$C_3$-alkyl, $C_1$-$C_3$-alkoxy and fluorinated $C_1$-$C_3$-alkoxy;
$R^{11}$ is selected from cyano; —$OR^{13}$; $NR^{14}R^{15}$; a 3-, 4-, 5-, 6- or 7-membered saturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated heterobicyclic ring containing 1, 2 or 3 heteroatoms or heteroatom groups selected from O, N, S, NO, SO and $SO_2$ as ring members, where the heteromoncyclic or heterobicyclic ring may carry 1, 2 or 3 substituents $R^{12}$; and as a substituent on a cycloalkyl ring, $R^{11}$ is additionally selected from $C_1$-$C_4$-alkyl and $C_1$-$C_4$-haloalkyl;
each $R^{12}$ is selected from halogen, cyano, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkyl, fluorinated $C_1$-$C_4$-alkoxy-$C_1$-$C_4$-alkyl, phenyl which may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy; and a 3-, 4-, 5- or 6-membered saturated heteromonocyclic ring containing 1, 2 or 3 heteroatoms or heteroatom groups selected from O, N, S, NO, SO and $SO_2$ as ring members, where the heteromonocyclic ring may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy;
$R^{13}$ is selected from hydrogen, $C_1$-$C_4$-alkyl and $C_1$-$C_4$-haloalkyl;
$R^{14}$ and $R^{15}$ are independently of each other selected from hydrogen and $C_1$-$C_4$-alkyl;
a is 0 or 1;
b is 0 or 1;
m and n are both 1 or 2; in particular 1; and
o and p are both 1 or 2; in particular 1.

The invention more preferably relates to compounds of the formula IA in which
$X^{5a}$ is N or CH;
$X^6$ is N or CH;
B is selected from phenyl, 2-pyridyl, 3-pyridyl and quinolin-8-yl, where B is unsubstituted or carries 1, 2 or 3 identical or different substituents $R^8$;
$R^1$ is hydrogen, chlorine or cyano; in particular cyano;
$R^2$ is hydrogen, fluorine or cyano; in particular hydrogen;
$R^5$ is selected from $C_1$-$C_6$-alkyl which carries one substituent $R^{11}$; a 3-, 4-, 5- or 6-membered saturated heteromonocyclic ring containing 1 or 2 heteroatoms or heteroatom groups selected from O, N, S, NO, SO and $SO_2$ as ring members; and a 5- or 6-membered heteroaromatic ring containing 1 or 2 heteroatoms selected from O, N and S as ring members, where the saturated heteromonocyclic or the heteroaromatic ring may carry 1, 2 or 3 substituents $R^{12}$;
$R^6$ is methoxy, ethoxy or 1,1-difluoroethyl;
$R^{7a}$ and $R^{7b}$, independently of each other, are hydrogen, fluorine or methoxy;

R$^8$ is selected from fluorine, chlorine, cyano, methyl, methoxy and trifluoromethoxy;

R$^{11}$ is a 4-, 5- or 6-membered, saturated heteromonocyclic ring containing 1 or 2 heteroatoms or heteroatom groups selected from O, N, S, NO, SO and SO$_2$ as ring members, where the heteromoncyclic ring may carry 1 or 2 or 3 substituents R$^{12}$;

R$^{12}$ is selected from C$_1$-C$_4$-alkyl, fluorinated C$_1$-C$_4$-alkyl, C$_1$-C$_4$-alkoxy-C$_1$-C$_4$-alkyl, fluorinated C$_1$-C$_4$-alkoxy-C$_1$-C$_4$-alkyl, and a 3-, 4-, 5- or 6-membered saturated heteromonocyclic ring containing 1 or 2 heteroatoms selected from O, N and S as ring members;

a is 0;
b is 0;
m and n are both 1 or 2; in particular 1; and
o and p are both 1 or 2; in particular 1.

In particular, the invention relates to compounds of the formula IA in which

X$^{5a}$ is N or CH;
X$^6$ is N or CH;
B is selected from phenyl, 2-pyridyl, 3-pyridyl and quinolin-8-yl, where B is unsubstituted or carries 1, 2 or 3 identical or different substituents R$^8$;
R$^1$ is hydrogen, chlorine or cyano; in particular cyano;
R$^2$ is hydrogen or cyano; in particular hydrogen;
R$^5$ is selected from C$_1$-C$_4$-alkyl which carries one substituent R$^{11}$; a 6-membered saturated heteromonocyclic ring containing 1 or 2 heteroatoms selected from O and N as ring members; and a 6-membered heteroaromatic ring containing 1 or 2 nitrogen atoms as ring members, where the saturated heteromonocyclic or the heteroaromatic ring may carry 1 or 2 substituents R$^{12}$;
R$^6$ is methoxy, ethoxy or 1,1-difluoroethyl;
R$^{7a}$ and R$^{7b}$ are hydrogen, fluorine or methoxy;
R$^8$ is fluorine, chlorine, cyano, methyl or methoxy;
R$^{11}$ is a 6-membered, saturated heteromonocyclic ring containing 1 or 2 heteroatoms or heteroatom groups selected from O, N, S, NO, SO and SO$_2$ as ring members, where the heteromoncyclic ring may carry 1 or 2 or 3 substituents R$^{12}$;
R$^{12}$ is selected from C$_1$-C$_4$-alkyl, fluorinated C$_1$-C$_4$-alkyl, C$_1$-C$_4$-alkoxy-C$_1$-C$_4$-alkyl, fluorinated C$_1$-C$_4$-alkoxy-C$_1$-C$_4$-alkyl, and a 3-, 4-, 5- or 6-membered saturated heteromonocyclic ring containing 1 or 2 heteroatoms selected from O, N and S as ring members;

a is 0;
b is 0;
m and n are both 1 or 2; in particular 1; and
o and p are both 1 or 2; in particular 1.

Examples of preferred embodiments of the present invention are compounds of the formulae I.1 to I.36 and the N-oxides, stereoisomers (inclusively the conformers) and the pharmaceutically acceptable salts thereof, in which the radicals R$^1$, R$^2$, R$^5$, R$^6$, R$^{7a}$ and R$^{7b}$ have one of the above general or preferred meanings. In particular, preferred compounds are the individual compounds compiled in the tables 1 to 648 below. Moreover, the meanings mentioned below for the individual variables in the tables are per se, independently of the combination in which they are mentioned, a particularly preferred embodiment of the substituents in question.

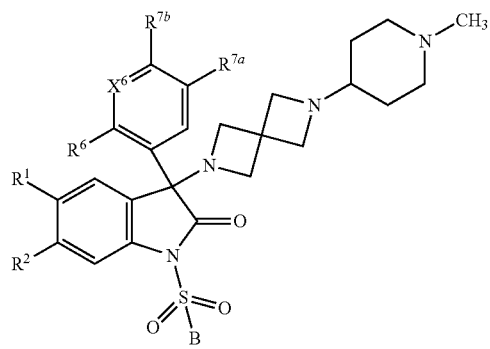

(I.1)

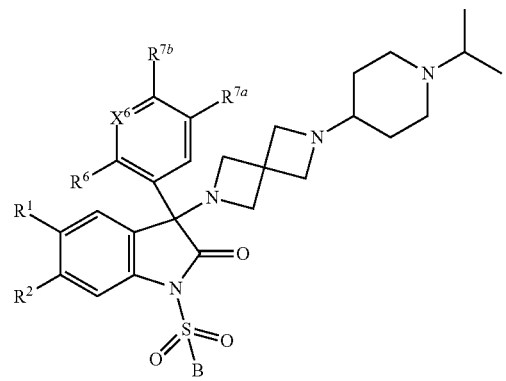

(I.2)

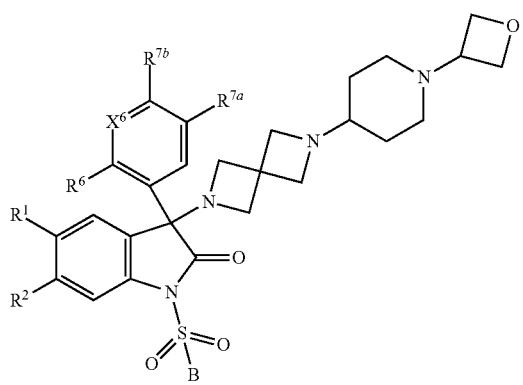

(I.3)

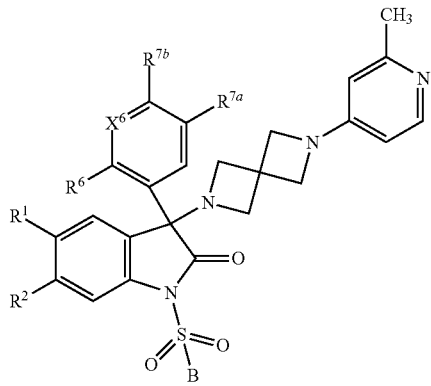

(I.4)

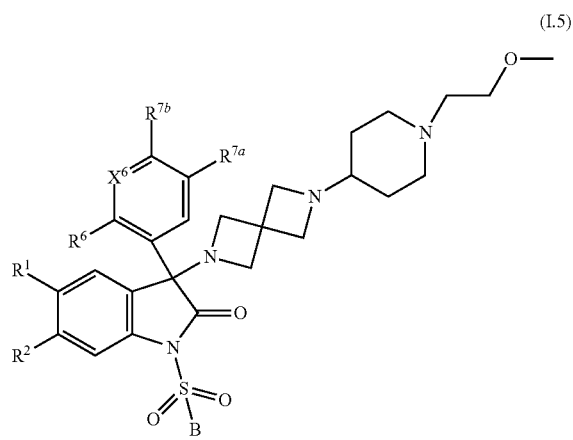
(I.5)
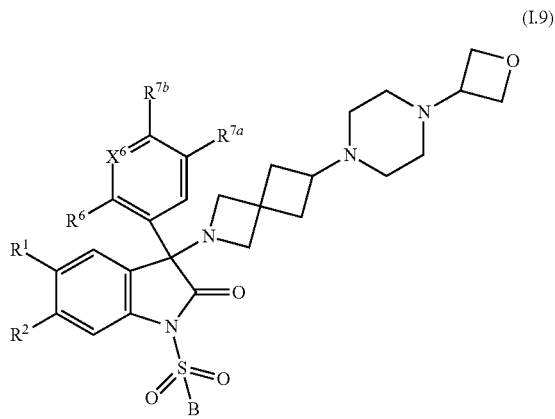
(I.9)
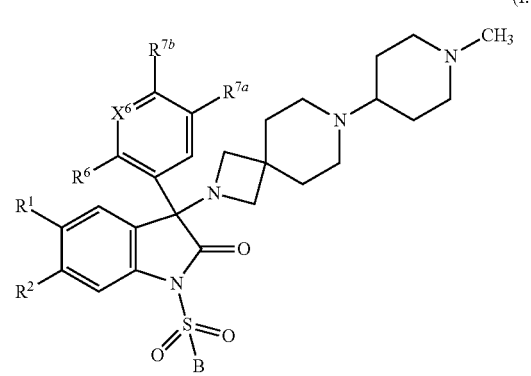
(I.6)
(I.10)
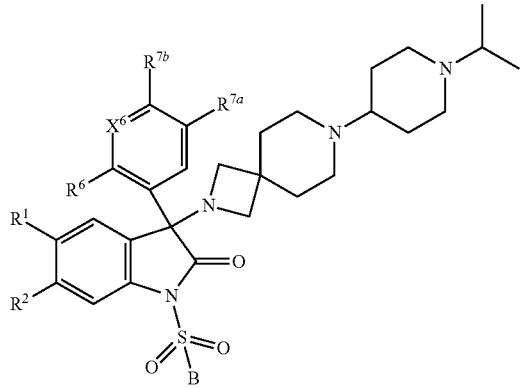
(I.7)
(I.11)
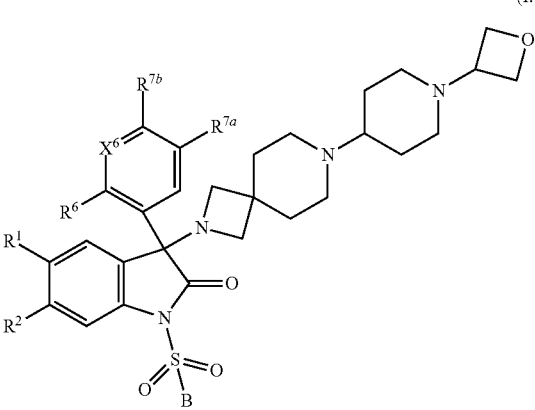
(I.8)
(I.12)

-continued
(I.13)
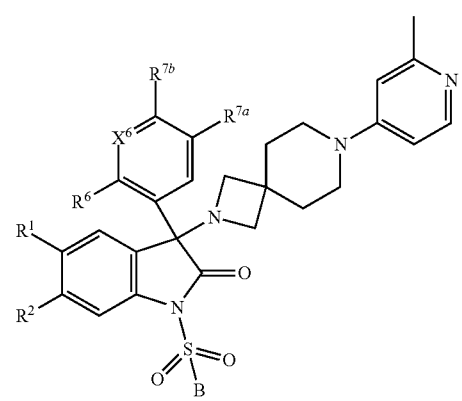
(I.14)
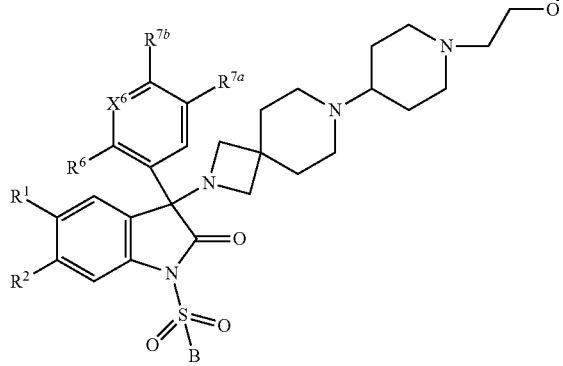
(I.15)
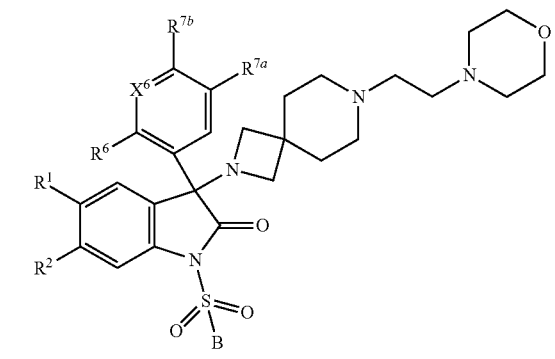
(I.16)
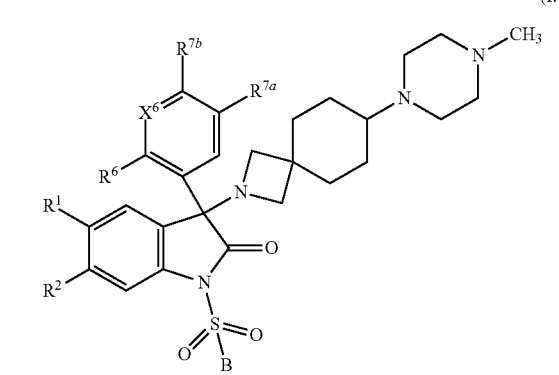
(I.17)
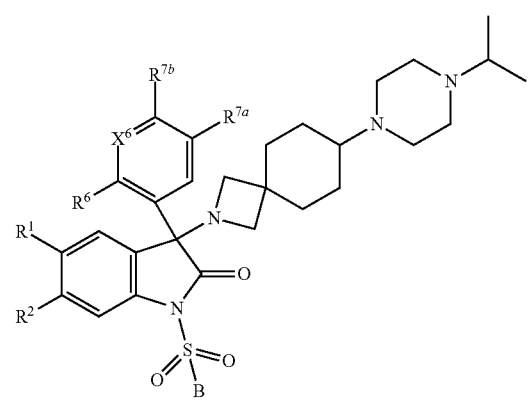
(I.18)
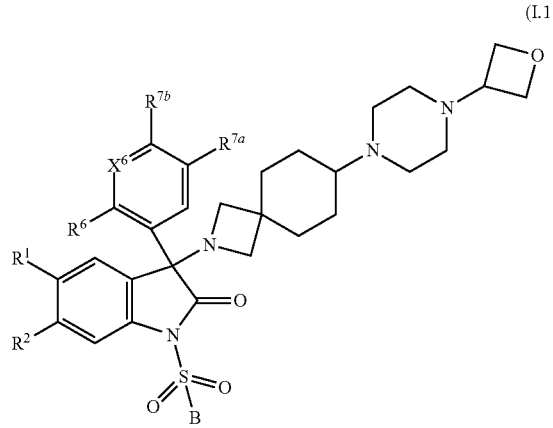
(I.19)
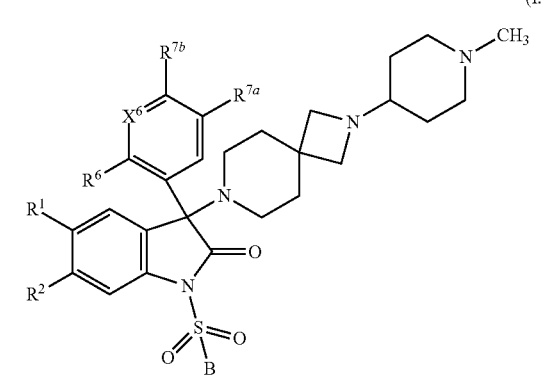
(I.20)
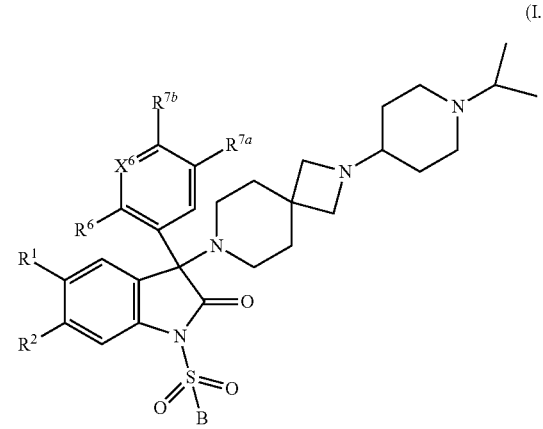

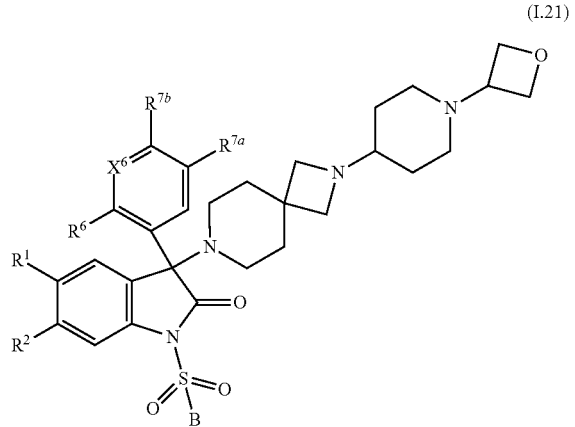
(I.21)
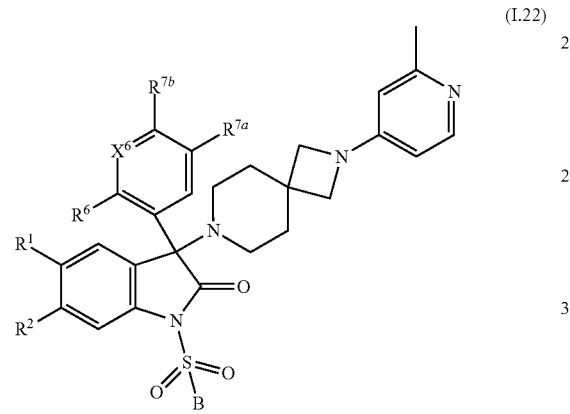
(I.22)
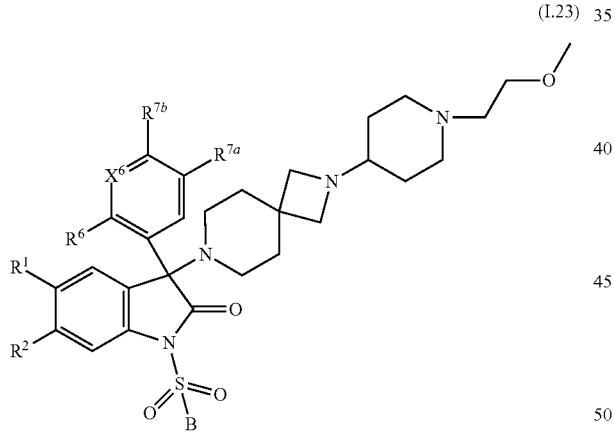
(I.23)
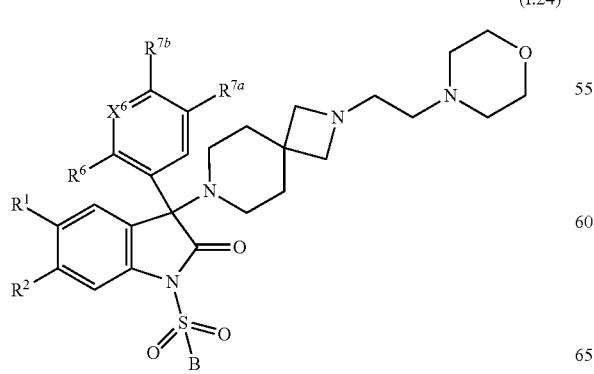
(I.24)
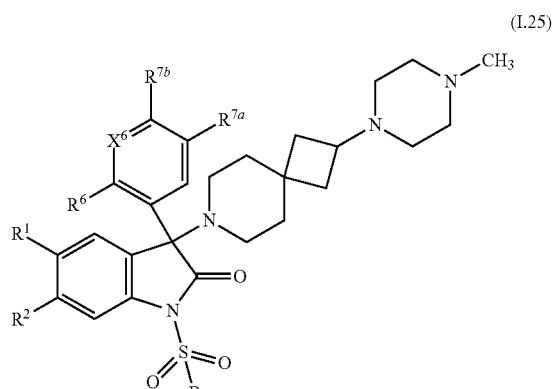
(I.25)
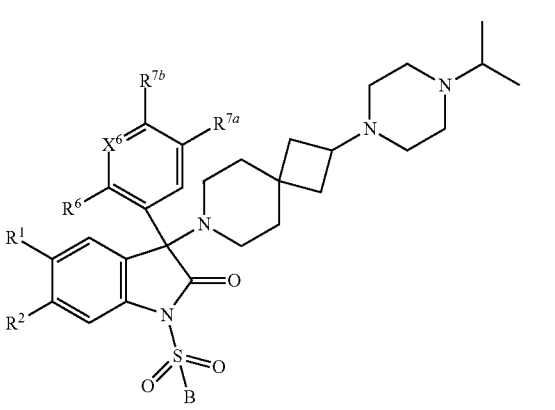
(I.26)
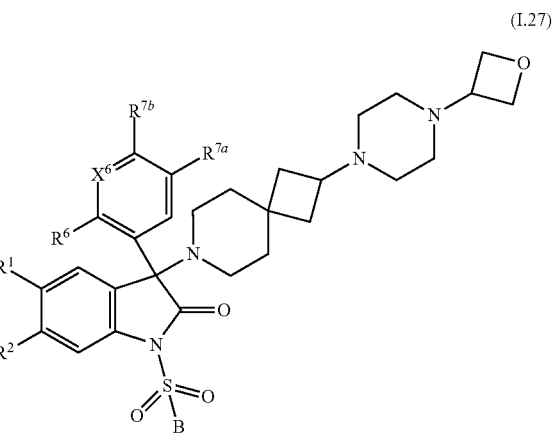
(I.27)
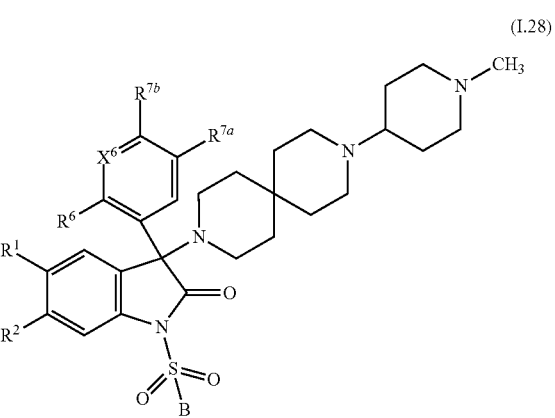
(I.28)

-continued
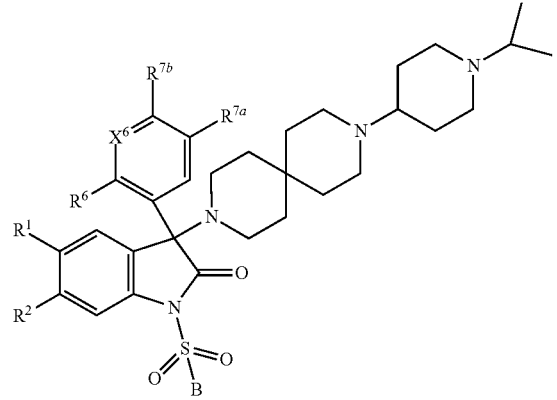
(I.29)
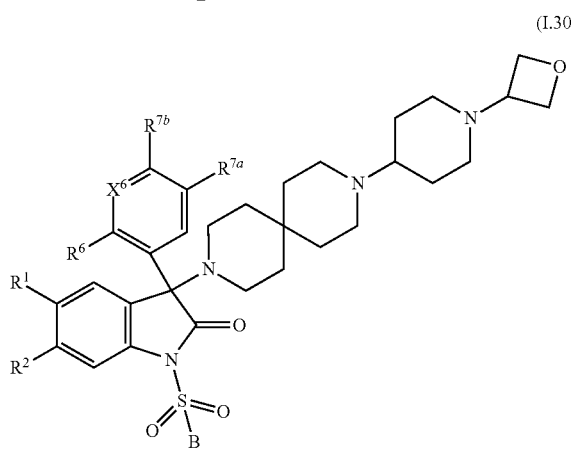
(I.30)
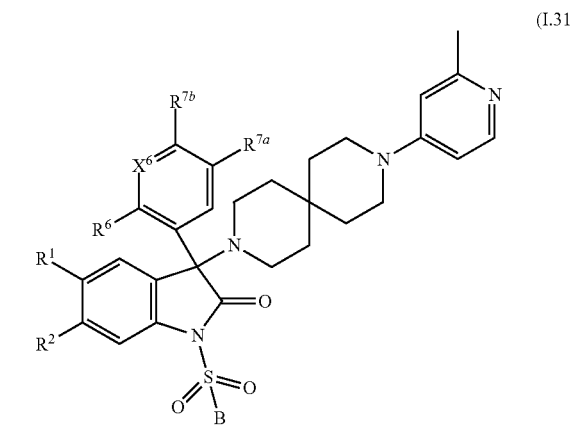
(I.31)
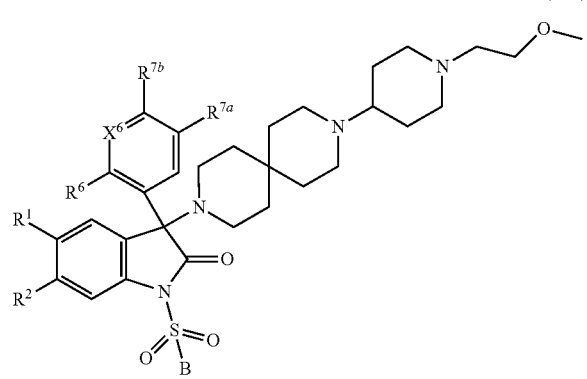
(I.32)
-continued
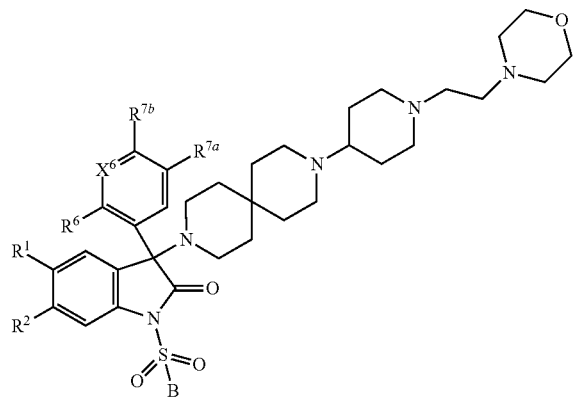
(I.33)
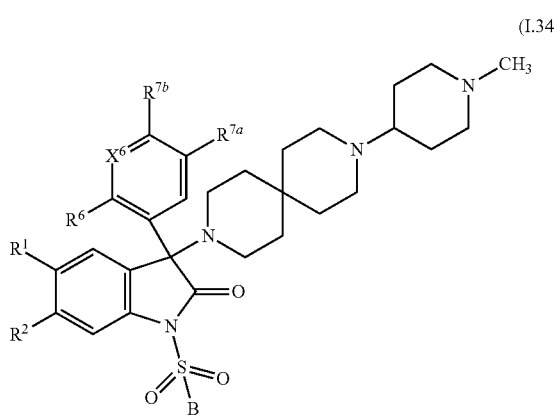
(I.34)
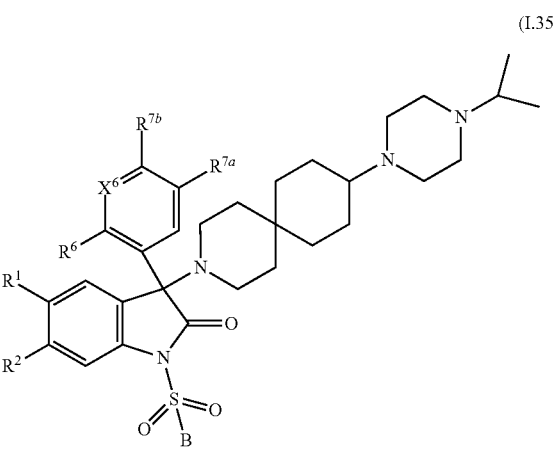
(I.35)

-continued (I.36)

[Chemical structure of formula I.36]

Table 1
Compounds of the formula I.1 in which B is 2-pyridyl, and $R^1$, $R^2$, $X^6$, $R^6$, $R^{7a}$ and $R^{7b}$ for a compound corresponds in each case to one row of Table A.

Table 2
Compounds of the formula I.1 in which B is 5-methyl-2-pyridyl, and $R^1$, $R^2$, $X^6$, $R^6$, $R^{7a}$ and $R^{7b}$ for a compound corresponds in each case to one row of Table A Table 3
Compounds of the formula I.1 in which B is 5-methoxy-2-pyridyl, and $R^1$, $R^2$, $X^6$, $R^6$, $R^{7a}$ and $R^{7b}$ for a compound corresponds in each case to one row of Table A.

Table 4
Compounds of the formula I.1 in which B is 5-chloro-2-pyridyl, and $R^1$, $R^2$, $X^6$, $R^6$, $R^{7a}$ and $R^{7b}$ for a compound corresponds in each case to one row of Table A.

Table 5
Compounds of the formula I.1 in which B is 6-methoxy-2-pyridyl, and $R^1$, $R^2$, $X^6$, $R^6$, $R^{7a}$ and $R^{7b}$ for a compound corresponds in each case to one row of Table A.

Table 6
Compounds of the formula I.1 in which B is 6-methoxy-3-pyridyl, and $R^1$, $R^2$, $X^6$, $R^6$, $R^{7a}$ and $R^{7b}$ for a compound corresponds in each case to one row of Table A.

Table 7
Compounds of the formula I.1 in which B is 8-quinolyl, and $R^1$, $R^2$, $X^6$, $R^6$, $R^{7a}$ and $R^{7b}$ for a compound corresponds in each case to one row of Table A.

Table 8
Compounds of the formula I.1 in which B is 5-methyl-8-quinolyl, and $R^1$, $R^2$, $X^6$, $R^6$, $R^{7a}$ and $R^{7b}$ for a compound corresponds in each case to one row of Table A.

Table 9
Compounds of the formula I.1 in which B is 5-methoxy-8-quinolyl, and $R^1$, $R^2$, $X^6$, $R^6$, $R^{7a}$ and $R^{7b}$ for a compound corresponds in each case to one row of Table A.

Table 10
Compounds of the formula I.1 in which B is 5-fluoro-8-quinolyl, and $R^1$, $R^2$, $X^6$, $R^6$, $R^{7a}$ and $R^{7b}$ for a compound corresponds in each case to one row of Table A.

Table 11
Compounds of the formula I.1 in which B is 4-methyl-8-quinolyl, and $R^1$, $R^2$, $X^6$, $R^6$, $R^{7a}$ and $R^{7b}$ for a compound corresponds in each case to one row of Table A.

Table 12
Compounds of the formula I.1 in which B is 4-ethyl-8-quinolyl, and $R^1$, $R^2$, $X^6$, $R^6$, $R^{7a}$ and $R^{7b}$ for a compound corresponds in each case to one row of Table A.

Table 13
Compounds of the formula I.1 in which B is 4-fluorophenyl, and $R^1$, $R^2$, $X^6$, $R^6$, $R^{7a}$ and $R^{7b}$ for a compound corresponds in each case to one row of Table A.

Table 14
Compounds of the formula I.1 in which B is 4-methylphenyl, and $R^1$, $R^2$, $X^6$, $R^6$, $R^{7a}$ and $R^{7b}$ for a compound corresponds in each case to one row of Table A.

Table 15
Compounds of the formula I.1 in which B is 4-methoxyphenyl, and $R^1$, $R^2$, $X^6$, $R^6$, $R^{7a}$ and $R^{7b}$ for a compound corresponds in each case to one row of Table A.

Table 16
Compounds of the formula I.1 in which B is 4-cyanophenyl, and $R^1$, $R^2$, $X^6$, $R^6$, $R^{7a}$ and $R^{7b}$ for a compound corresponds in each case to one row of Table A.

Table 17
Compounds of the formula I.1 in which B is 2-methoxyphenyl, and $R^1$, $R^2$, $X^6$, $R^6$, $R^{7a}$ and $R^{7b}$ for a compound corresponds in each case to one row of Table A.

Table 18
Compounds of the formula I.1 in which B is 2,4-dimethoxyphenyl, and $R^1$, $R^2$, $X^6$, $R^6$, $R^{7a}$ and $R^{7b}$ for a compound corresponds in each case to one row of Table A.

Tables 19 to 36
Compounds of the formula I.2 in which B is as defined in tables 1 to 18 and the combination $R^1$, $R^2$, $X^6$, $R^6$, $R^{7a}$ and $R^{7b}$ for a compound corresponds in each case to one row of Table A.

Tables 37 to 54
Compounds of the formula I.3 in which B is as defined in tables 1 to 18 and the combination $R^1$, $R^2$, $X^6$, $R^6$, $R^{7a}$ and $R^{7b}$ for a compound corresponds in each case to one row of Table A.

Tables 55 to 72
Compounds of the formula I.4 in which B is as defined in tables 1 to 18 and the combination $R^1$, $R^2$, $X^6$, $R^6$, $R^{7a}$ and $R^{7b}$ for a compound corresponds in each case to one row of Table A.

Tables 73 to 90
Compounds of the formula I.5 in which B is as defined in tables 1 to 18 and the combination $R^1$, $R^2$, $X^6$, $R^6$, $R^{7a}$ and $R^{7b}$ for a compound corresponds in each case to one row of Table A.

Tables 91 to 108
Compounds of the formula I.6 in which B is as defined in tables 1 to 18 and the combination $R^1$, $R^2$, $X^6$, $R^6$, $R^{7a}$ and $R^{7b}$ for a compound corresponds in each case to one row of Table A.

Tables 109 to 126
Compounds of the formula I.7 in which B is as defined in tables 1 to 18 and the combination $R^1$, $R^2$, $X^6$, $R^6$, $R^{7a}$ and $R^{7b}$ for a compound corresponds in each case to one row of Table A.

Tables 127 to 144
Compounds of the formula I.8 in which B is as defined in tables 1 to 18 and the combination $R^1$, $R^2$, $X^6$, $R^6$, $R^{7a}$ and $R^{7b}$ for a compound corresponds in each case to one row of Table A.

Tables 145 to 162
Compounds of the formula I.9 in which B is as defined in tables 1 to 18 and the combination $R^1$, $R^2$, $X^6$, $R^6$, $R^{7a}$ and $R^{7b}$ for a compound corresponds in each case to one row of Table A.

Tables 163 to 180
Compounds of the formula I.10 in which B is as defined in tables 1 to 18 and the combination $R^1$, $R^2$, $X^6$, $R^6$, $R^{7a}$ and $R^{7b}$ for a compound corresponds in each case to one row of Table A.

Tables 181 to 198
Compounds of the formula I.11 in which B is as defined in tables 1 to 18 and the combination $R^1$, $R^2$, $X^6$, $R^6$, $R^{7a}$ and $R^{7b}$ for a compound corresponds in each case to one row of Table A.

Tables 199 to 216
Compounds of the formula I.12 in which B is as defined in tables 1 to 18 and the combination $R^1$, $R^2$, $X^6$, $R^6$, $R^{7a}$ and $R^{7b}$ for a compound corresponds in each case to one row of Table A.

Tables 217 to 234
Compounds of the formula I.13 in which B is as defined in tables 1 to 18 and the combination $R^1$, $R^2$, $X^6$, $R^6$, $R^{7a}$ and $R^{7b}$ for a compound corresponds in each case to one row of Table A.

Tables 235 to 252
Compounds of the formula I.14 in which B is as defined in tables 1 to 18 and the combination $R^1$, $R^2$, $X^6$, $R^6$, $R^{7a}$ and $R^{7b}$ for a compound corresponds in each case to one row of Table A.

Tables 253 to 270
Compounds of the formula I.15 in which B is as defined in tables 1 to 18 and the combination $R^1$, $R^2$, $X^6$, $R^6$, $R^{7a}$ and $R^{7b}$ for a compound corresponds in each case to one row of Table A.

Tables 271 to 288
Compounds of the formula I.16 in which B is as defined in tables 1 to 18 and the combination $R^1$, $R^2$, $X^6$, $R^6$, $R^{7a}$ and $R^{7b}$ for a compound corresponds in each case to one row of Table A.

Tables 289 to 306
Compounds of the formula I.17 in which B is as defined in tables 1 to 18 and the combination $R^1$, $R^2$, $X^6$, $R^6$, $R^{7a}$ and $R^{7b}$ for a compound corresponds in each case to one row of Table A.

Tables 307 to 324
Compounds of the formula I.18 in which B is as defined in tables 1 to 18 and the combination $R^1$, $R^2$, $X^6$, $R^6$, $R^{7a}$ and $R^{7b}$ for a compound corresponds in each case to one row of Table A.

Tables 325 to 342
Compounds of the formula I.19 in which B is as defined in tables 1 to 18 and the combination $R^1$, $R^2$, $X^6$, $R^6$, $R^{7a}$ and $R^{7b}$ for a compound corresponds in each case to one row of Table A.

Tables 343 to 360
Compounds of the formula I.20 in which B is as defined in tables 1 to 18 and the combination $R^1$, $R^2$, $X^6$, $R^6$, $R^{7a}$ and $R^{7b}$ for a compound corresponds in each case to one row of Table A.

Tables 361 to 378
Compounds of the formula I.21 in which B is as defined in tables 1 to 18 and the combination $R^1$, $R^2$, $X^6$, $R^6$, $R^{7a}$ and $R^{7b}$ for a compound corresponds in each case to one row of Table A.

Tables 379 to 396
Compounds of the formula I.22 in which B is as defined in tables 1 to 18 and the combination $R^1$, $R^2$, $X^6$, $R^6$, $R^{7a}$ and $R^{7b}$ for a compound corresponds in each case to one row of Table A.

Tables 397 to 414
Compounds of the formula I.23 in which B is as defined in tables 1 to 18 and the combination $R^1$, $R^2$, $X^6$, $R^6$, $R^{7a}$ and $R^{7b}$ for a compound corresponds in each case to one row of Table A.

Tables 415 to 432
Compounds of the formula I.24 in which B is as defined in tables 1 to 18 and the combination $R^1$, $R^2$, $X^6$, $R^6$, $R^{7a}$ and $R^{7b}$ for a compound corresponds in each case to one row of Table A.

Tables 433 to 450
Compounds of the formula I.25 in which B is as defined in tables 1 to 18 and the combination $R^1$, $R^2$, $X^6$, $R^6$, $R^{7a}$ and $R^{7b}$ for a compound corresponds in each case to one row of Table A.

Tables 451 to 468
Compounds of the formula I.26 in which B is as defined in tables 1 to 18 and the combination $R^1$, $R^2$, $X^6$, $R^6$, $R^{7a}$ and $R^{7b}$ for a compound corresponds in each case to one row of Table A.

Tables 469 to 486
Compounds of the formula I.27 in which B is as defined in tables 1 to 18 and the combination $R^1$, $R^2$, $X^6$, $R^6$, $R^{7a}$ and $R^{7b}$ for a compound corresponds in each case to one row of Table A.

Tables 487 to 504
Compounds of the formula I.28 in which B is as defined in tables 1 to 18 and the combination $R^1$, $R^2$, $X^6$, $R^6$, $R^{7a}$ and $R^{7b}$ for a compound corresponds in each case to one row of Table A.

Tables 505 to 522
Compounds of the formula I.29 in which B is as defined in tables 1 to 18 and the combination $R^1$, $R^2$, $X^6$, $R^6$, $R^{7a}$ and $R^{7b}$ for a compound corresponds in each case to one row of Table A.

Tables 523 to 540
Compounds of the formula I.30 in which B is as defined in tables 1 to 18 and the combination $R^1$, $R^2$, $X^6$, $R^6$, $R^{7a}$ and $R^{7b}$ for a compound corresponds in each case to one row of Table A.

Tables 541 to 558
Compounds of the formula I.31 in which B is as defined in tables 1 to 18 and the combination $R^1$, $R^2$, $X^6$, $R^6$, $R^{7a}$ and $R^{7b}$ for a compound corresponds in each case to one row of Table A.

Tables 559 to 576
Compounds of the formula I.32 in which B is as defined in tables 1 to 18 and the combination $R^1$, $R^2$, $X^6$, $R^6$, $R^{7a}$ and $R^{7b}$ for a compound corresponds in each case to one row of Table A.

Tables 577 to 594
Compounds of the formula I.33 in which B is as defined in tables 1 to 18 and the combination $R^1$, $R^2$, $X^6$, $R^6$, $R^{7a}$ and $R^{7b}$ for a compound corresponds in each case to one row of Table A.

Tables 595 to 612
Compounds of the formula I.34 in which B is as defined in tables 1 to 18 and the combination $R^1$, $R^2$, $X^6$, $R^6$, $R^{7a}$ and $R^{7b}$ for a compound corresponds in each case to one row of Table A.

Tables 613 to 630
Compounds of the formula I.35 in which B is as defined in tables 1 to 18 and the combination $R^1$, $R^2$, $X^6$, $R^6$, $R^{7a}$ and $R^{7b}$ for a compound corresponds in each case to one row of Table A.

Tables 631 to 648

Compounds of the formula I.36 in which B is as defined in tables 1 to 18 and the combination $R^1$, $R^2$, $X^6$, $R^6$, $R^{7a}$ and $R^{7b}$ for a compound corresponds in each case to one row of Table A.

TABLE A

| Example No. | $R^1$ | $R^2$ | $X^6$ | $R^6$ | $R^{7a}$ | $R^{7b}$ |
|---|---|---|---|---|---|---|
| A-1. | CN | H | N | $CF_2CH_3$ | H | H |
| A-2. | H | CN | N | $CF_2CH_3$ | H | H |
| A-3. | Cl | H | N | $CF_2CH_3$ | H | H |
| A-4. | H | H | N | $CF_2CH_3$ | H | H |
| A-5. | CN | H | N | $OC_2H_5$ | H | H |
| A-6. | H | CN | N | $OC_2H_5$ | H | H |
| A-7. | Cl | H | N | $OC_2H_5$ | H | H |
| A-8. | H | H | N | $OC_2H_5$ | H | H |
| A-9. | CN | H | N | $OCH_3$ | H | H |
| A-10. | H | CN | N | $OCH_3$ | H | H |
| A-11. | Cl | H | N | $OCH_3$ | H | H |
| A-12. | H | H | N | $OCH_3$ | H | H |
| A-13. | CN | H | N | $OC_2H_5$ | H | Cl |
| A-14. | H | CN | N | $OC_2H_5$ | H | Cl |
| A-15. | Cl | H | N | $OC_2H_5$ | H | Cl |
| A-16. | H | H | N | $OC_2H_5$ | H | Cl |
| A-17. | CN | H | N | $OCH_3$ | H | Cl |
| A-18. | H | CN | N | $OCH_3$ | H | Cl |
| A-19. | Cl | H | N | $OCH_3$ | H | Cl |
| A-20. | H | H | N | $OCH_3$ | H | Cl |
| A-21. | CN | H | CH | $OCH_3$ | H | H |
| A-22. | H | CN | CH | $OCH_3$ | H | H |
| A-23. | Cl | H | CH | $OCH_3$ | H | H |
| A-24. | H | H | CH | $OCH_3$ | H | H |
| A-25. | CN | H | CH | $OC_2H_5$ | H | H |
| A-26. | H | CN | CH | $OC_2H_5$ | H | H |
| A-27. | Cl | H | CH | $OC_2H_5$ | H | H |
| A-28. | H | H | CH | $OC_2H_5$ | H | H |
| A-29. | CN | H | CH | Cl | H | H |
| A-30. | H | CN | CH | Cl | H | H |
| A-31. | Cl | H | CH | Cl | H | H |
| A-32. | H | H | CH | Cl | H | H |
| A-33. | CN | H | CH | $OCH_3$ | $OCH_3$ | H |
| A-34. | H | CN | CH | $OCH_3$ | $OCH_3$ | H |
| A-35. | Cl | H | CH | $OCH_3$ | $OCH_3$ | H |
| A-36. | H | H | CH | $OCH_3$ | $OCH_3$ | H |
| A-37. | CN | H | CH | $OCH_3$ | $OC_2H_5$ | H |
| A-38. | H | CN | CH | $OCH_3$ | $OC_2H_5$ | H |
| A-39. | Cl | H | CH | $OCH_3$ | $OC_2H_5$ | H |
| A-40. | H | H | CH | $OCH_3$ | $OC_2H_5$ | H |
| A-41. | CN | H | CH | $OC_2H_5$ | $OCH_3$ | H |
| A-42. | H | CN | CH | $OC_2H_5$ | $OCH_3$ | H |
| A-43. | Cl | H | CH | $OC_2H_5$ | $OCH_3$ | H |
| A-44. | H | H | CH | $OC_2H_5$ | $OCH_3$ | H |
| A-45. | CN | H | CH | $OCH_3$ | $CH_3$ | H |
| A-46. | H | CN | CH | $OCH_3$ | $CH_3$ | H |
| A-47. | Cl | H | CH | $OCH_3$ | $CH_3$ | H |
| A-48. | H | H | CH | $OCH_3$ | $CH_3$ | H |
| A-49. | CN | H | CH | $OCH_3$ | H | $OCH_3$ |
| A-50. | H | CN | CH | $OCH_3$ | H | $OCH_3$ |
| A-51. | Cl | H | CH | $OCH_3$ | H | $OCH_3$ |
| A-52. | H | H | CH | $OCH_3$ | H | $OCH_3$ |
| A-53. | CN | H | CH | $OC_2H_5$ | H | $OCH_3$ |
| A-54. | H | CN | CH | $OC_2H_5$ | H | $OCH_3$ |
| A-55. | Cl | H | CH | $OC_2H_5$ | H | $OCH_3$ |
| A-56. | H | H | CH | $OC_2H_5$ | H | $OCH_3$ |
| A-57. | CN | H | CH | $OC_2H_5$ | H | F |
| A-58. | H | CN | CH | $OC_2H_5$ | H | F |
| A-59. | Cl | H | CH | $OC_2H_5$ | H | F |
| A-60. | H | H | CH | $OC_2H_5$ | H | F |
| A-61. | CN | H | CH | $OC_2H_5$ | $CH_3$ | H |
| A-62. | H | CN | CH | $OC_2H_5$ | $CH_3$ | H |
| A-63. | Cl | H | CH | $OC_2H_5$ | $CH_3$ | H |
| A-64. | H | H | CH | $OC_2H_5$ | $CH_3$ | H |
| A-65. | CN | H | CH | $OC_2H_5$ | $C_2H_5$ | H |
| A-66. | H | CN | CH | $OC_2H_5$ | $C_2H_5$ | H |
| A-61. | Cl | H | CH | $OC_2H_5$ | $C_2H_5$ | H |
| A-68. | H | H | CH | $OC_2H_5$ | $C_2H_5$ | H |

The particularly preferred compounds among the compounds I.1 to I.36 mentioned above are those of the formula I.1, I.2, I.3, I.4, I.5, I.6, I.7, I.8 and I.9, in particular I.1.

In a specific embodiment, the compounds I are selected from the compounds specified in the examples, either as a free base or in form of a pharmaceutically acceptable salt, an N-oxide or a stereoisomer or the racemate or any mixture of stereoisomers thereof.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts of the pure enantiomers of compounds I, and the mixtures of enantiomers in the form of the pharmaceutically acceptable salts of compounds I.

Preferred embodiments of the invention are compounds of the formula I as detailed above which are characterized in that they are in optically active form, and the enantiomer of the relevant compound of the formula I is the S-enantiomer, in the form of a free base, or a pharmaceutically acceptable salt thereof.

Particularly preference is given to compounds of the general formula I and their pharmaceutically acceptable salts as detailed above in which the corresponding S-enantiomer is present in an optical purity (enantiomeric excess, ee) of more than 50% ee, particularly preferably of at least 80% ee, more preferably of at least 90% ee and even more preferably of at least 95% ee and in particular of at least 98% ee.

Likewise preferred embodiments of the invention are compounds of the general formula I as detailed above which are characterized in that they are in optically inactive form, i.e. in the form of the racemate, or in the form of a pharmaceutically acceptable salt of the racemate.

The compounds of the invention can be prepared by using methods described in WO 2008/025735 and WO 2008/107399 for synthesizing analogous compounds, and the preparation is outlined by way of example in synthesis scheme 1 and also in the experimental part below. If not indicated otherwise, the variables in these synthetic schemes have the same meanings as in formula I.

Scheme 1:

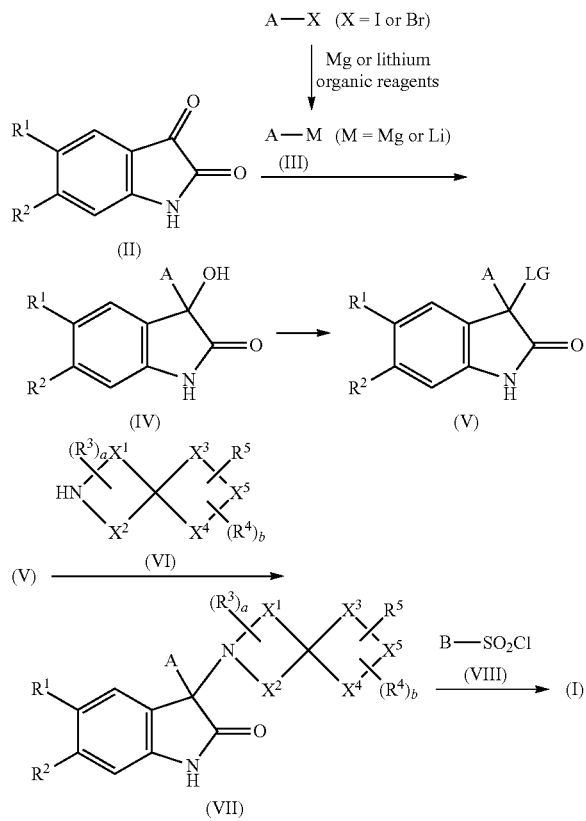

In scheme 1, LG means a leaving group, such as chlorine or bromine. The 3-hydroxy-1,3-dihydroindol-2-ones IV can be obtained by addition of metallated benzenes or heterocycles III onto the 3-keto group of the isatins II. The metallated benzenes or heterocycles, such as, for example, the corresponding Grignard (Mg) or organyllithium compound, can be obtained in any conventional way from halogen or hydrocarbon compounds. Examples of methods are present in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV which comprise an iodine in the 6-membered aromatic ring, for example in position 5 or 6, i.e. in the position of the radicals $R^1$ or $R^2$, can be converted with KCN or $Zn(CN)_2$ with Pd(0) catalysis in solvents such as dimethylformamide or tetrahydrofuran, where appropriate also with addition of bases such as $K_2CO_3$ or other carbonates or amines, at elevated temperature into the analogous cyan-containing 3-hydroxyoxindole IV. Pd(0) salts which can be taken are for example transition metal complexes which are prepared in situ from $PdCl_2$ or $PdOAc_2$ by addition of phosphines such as tris(orthotolyl) phosphine. It is likewise possible to employ commercial palladium complexes such as, for example, the catalyst tetrakis(triphenylphosphine)palladium(0) and/or additions of phosphine ligands.

The 3-hydroxyoxindoles IV can be converted into the compounds V which have a leaving group LG in position 3, where the leaving group LG is a conventional leaving group such as, for example, chlorine or bromide. The intermediate V with for example LG=chlorine can be prepared by treating the alcohol IV with thionyl chloride in the presence of a base such as, for example, pyridine, in a suitable solvent such as, for example, dichloromethane. The compounds V can subsequently be reacted with an amine VI, to give the amine VII. Spiro compounds VI can be used in protected form, if required, e.g. if one of $X^1$, $X^2$, $X^3$, $X^4$ and/or $X^5$ is NH and is not substituted by a radical $R^3$, $R^4$ or $R^5$ which confers protection to this nitrogen ring atom. Suitable protective groups are, for example, $C_1$-$C_4$-alkoxycarbonyl groups, such as tert-butoxycarbonyl (Boc), $C_1$-$C_4$-alkylcarbonyl groups, such as acetyl, $C_1$-$C_4$-alkylsulfonyl, phenylsulfonyl or benzyl. Usually, Boc is used. The Boc protective group can subsequently be removed, for example by treatment with trifluoroacetic acid in dichloromethane. The compounds VII can subsequently be converted by treatment with sulfonyl chlorides VIII after deprotonation with a strong base such as, for example, potassium tertbutoxide or sodium hydride in DMF into the compound of formula I. The spiro compound VI employed can either be purchased or be prepared by known processes. The sulfonyl chlorides VII employed can either be purchased or be prepared by known processes (for example J. Med. Chem. 40, 1149 (1997) or WO 2008/107399).

Moreover, radical $R^5$ (if not hydrogen) can be introduced at a later point of time, especially if bound to $X^5$. For example, a compound I, where $X^5$—$R^5$ together are $NR^5$, can be prepared by treating a compound I, where $X^5$—$R^5$ together are NH, with a suitable precursor compound of $R^5$ (especially if $R^5$ is optionally substituted alkyl or a 3-, 4-, 5- or 6-membered saturated heteromonocyclic ring containing 1 or 2 heteroatoms or heteroatom groups selected from O, N, S, NO, SO and $SO_2$ as ring members), such as $R^5$=Y wherein Y is an oxo group (=O), in the sense of a reductive amination reaction in the presence of a reducing agent such as sodium cyanoborohydride. Phenyl or heterocyclyl groups $R^5$ can be introduced in a Buchwald-Hartwig reaction using a Pd catalyst.

The sequence of reaction steps can be varied. For instance, in scheme 1, the (het)arylsulfonyl group B—$SO_2$— can be introduced earlier than shown, e.g. by reacting yet II, IV or V with VIII in scheme 1.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the unlabeled compounds according to the invention might naturally include certain amounts of these respective isotopes. Therefore, when referring to compounds I, wherein at least one of the atoms has been replaced by its stable, non-radioactive isotope, it will be understood that the isotope is present in a higher amount than would naturally occur.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J.

Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as D2SO4/D2O. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO 1997010223, WO20050993 53, WO 1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

Affective disorders have been related to excessive vasopressin function. Therefore, treatment with compounds targeting the vasopressin system, such as vasopressin antagonists are likely to benefit patients suffering from affective disorders (see for example Surget A., Belzung C., Involvement of vasopressin in affective disorders, Eur. J. Pharm. 2008, 583, 340-349). Affective disorders (mood disorders) include depressive disorders, anxiety disorders, obsessive-compulsive and related disorders, trauma and stressor-related disorders as well as bipolar and related disorders. V1b antagonist have been shown to have anti-drug abuse effects and reduce drug withdrawal effect (see e.g. Zhou Y., Leri F., Cummins E., Hoeschele M., Kreek M. J., Involvement of arginine vasopressin and V1b receptor in heroin withdrawal and heroin seeking precipitated by stress and by heroin. Neuropsychopharmacology, 2008, 33, 226-236). Therefore, compounds targeting the vasopressin system, such as vasopressin antagonists, are thought to be effective for treatment of substance-related and addictive disorders. V1b receptors play a role in a range of emotional responses such as aggression. Attenuating V1b receptor function genetically or with antagonist reduces aggressive behavior (Blanchard R. J., Griebel G., Farrokhi C., Markham C., Yang M., Blanchard D. C., AVP V1b selective antagonist SSR149415 blocks aggressive behaviors in hamsters. Pharmacol. Biochem. Behav. 2005, 80, 189-194; Wersinger S. R., Ginns E. I., O'Carroll A. M., Lolait S. J., Young W. S., III, Vasopressin V1b receptor knockout reduces aggressive behavior in male mice. Mol. Psychiatry, 2002, 7, 975-984). Therefore, attenuating V1b antagonists functioning is likely to reduce aggression and agitation in disorders such as Alzheimer's disease and schizophrenia and other psychiatric and neurological disorders in which aggressive behavior occurs, such as Alzheimer's disease, schizophrenia, bipolar disorder, frontal lobe injuries or substance use disorders.

High cortisol levels have been correlated to reduced cognitive performance in elderly and AD (Alzheimer's disease) patients, and such correlations are more pronounced in subjects carrying the APOε4 allele, which is a risk factor for AD (see for example Lee B. K., Glass T. A., Wand G. S., McAtee M. J., Bandeen-Roche K., Bolla K. I., Schwartz B. S., Apolipoprotein e genotype, cortisol, and cognitive function in community-dwelling older adults. Am. J. Psychiatry 2008, 165, 1456-1464). Furthermore, increased plasma cortisol has been associated with more rapid disease progression in AD patients. Animal studies show an interaction between glucocorticoids and AD pathology, including amyloid precursor protein and tau accumulation (see for example Budas G., Coughlan C. M., Seckl J. R., Breen K. C., The effect of corticosteroids on amyloid beta precursor protein/amyloid precursor-like protein expression and processing in vivo. Neurosci. Lett., 1999, 276, 61-64). Cognitive performance can be impaired by stress or exposure to high doses of corticosterone in laboratory animals (for review see Roozendaal B., Systems mediating acute glucocorticoid effects on memory consolidation and retrieval. Prog. Neuropsychopharmacol. Biol. Psychiatry, 2003, 27, 1213-1223). Therefore, lowering cortisol by treatment with V1b antagonist may enhance cognition or prevent/slow down the pathology or cognitive decline Alzheimer's disease patients and in patients with other cognitive impairment such as schizophrenia and depression.

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition; as well as to compounds of the invention of the formula I or of an N-oxide, a stereoisomer or of pharmaceutically acceptable salts thereof for the treatment and/or prophylaxis of the above-listed diseases. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness; as well as to compounds of the invention of the formula I or of an N-oxide, a stereoisomer or of pharmaceutically acceptable salts thereof for the treatment and/or prophylaxis of the above-listed diseases.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders, anxiety disorders, obsessive-compulsive and related disorders, trauma and stressor-related disorders, and bipolar and related disorders. Depressive disorders include for example dysthymic disorders, major depression, seasonal depression, treatment-resistant depression disorders, disruptive mood dysregulation disorder, premenstrual dysphoric disorder, substance/medication-induced depressive disorder, depressive disorder due to another medical condition, or childhood onset mood disorders. Anxiety disorders include for example phobias, specific phobias, general anxiety disorders, panic disorders, drug withdrawal-induced anxiety disorders, separation anxiety disorder, selective mutism, social anxiety disorder, agoraphobia, substance/medication-induced anxiety disorder and anxiety disorder due to another medical condition. Obsessive-compulsive and related disorders include for example obsessive-compulsive disorder, body dysmorphic disorder, hoarding disorder, trichotillomania, excoriation disorder, substance/medication-induced obsessive-compulsive and related disorder and other specified obsessive-compulsive and related disorders. Trauma and stressor-related disorders include for example reactive attachment disorder, disinhibited social engagement disorder, post-traumatic stress disorder, acute stress disorder, adjustment disorder and other specified trauma- and stressor-related disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, specific phobias, post-traumatic anxiety disorders, panic anxiety disorders, obsessive-compulsive anxiety disorders, acute stress-dependent anxiety disorders, drug withdrawal-induced anxiety disorders, separation anxiety disorder, selective mutism, social anxiety disorder, agoraphobia, substance/medication-induced anxiety disorder and anxiety disorder due to another medical condition and social phobia. The compounds of the invention of the formula I and their N-oxides, a stereoisomers or pharmaceutically acceptable salts or the pharmaceutical composition of the invention can likewise be employed for the treatment of obsessive-compulsive and related disorders, including, for example, obsessive-compulsive disorder, body dysmorphic disorder, hoarding disorder, trichotillomania, excoriation disorder, substance/medication-induced obsessive-compulsive and related disorder and other specified obsessive-compulsive and related disorders. The compounds of the invention of the formula I and their N-oxides, a stereoisomers or pharmaceutically acceptable salts or the pharmaceutical composition of the invention can likewise be employed for the treatment of trauma and stressor-related disorders, including, for example, reactive attachment disorder, disinhibited social engagement disorder, post-traumatic stress disorder, acute stress disorder, adjustment disorder and other specified trauma- and stressor-related disorders.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions selected from Alzheimer's disease, schizophrenia, bipolar disorder, frontal lobe injuries and substance use disorders.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders; as well as to compounds of the invention of the formula I or of an N-oxide, a stereoisomer or of pharmaceutically acceptable salts thereof for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders; as well as to compounds of the invention of the formula I or of an N-oxide, a stereoisomer or of pharmaceutically acceptable salts thereof for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders; as well as to compounds of the invention of the formula I or of an N-oxide, a stereoisomer or of pharmaceutically acceptable salts thereof for the treatment and/or prophylaxis of depressive disorders. In the case of depressive disorders, specific mention is to be made of childhood onset mood disorders, i.e. depressive moods having their onset in childhood, but also of major depression, seasonal depression, bipolar and related disorders, dysthymic disorders, disruptive mood dysregulation disorder, premenstrual dysphoric disorder, substance/medication-induced depressive disorder, and depressive disorder due to another medical condition, and especially of major depression and seasonal depression as well as of the depressive phases of bipolar disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors; as well as to compounds of the invention of the formula I or of an N-oxide, a stereoisomer or of pharmaceutically acceptable salts thereof for the treatment and/or prophylaxis of the above-listed diseases. To be more precise, the present invention relates to the use of compounds of the invention of the formula I or of an N-oxide, a stereoisomer or pharmaceutically acceptable salts thereof for the manufacture of a medicament for the treatment and/or prophylaxis of substance-related and addictive disorders such as substance use disorder, substance-induced disorder, alcohol use disorder, alcohol intoxication, alcohol withdrawal, unspecified alcohol-related disorder, caffeine intoxication, caffeine withdrawal, unspecified caffeine disorder, cannabis use disorder, cannabis withdrawal, unspecified cannabis-related disorder, phencyclidine use disorder, other hallucinogen use disorders, phencyclidine intoxication, other hallucinogen disorders, hallucinogen persisting perception disorder, unspecified phencyclidine disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, unspecified tobacco-related disorder, other (or unknown) substance use disorders, other (or unknown) substance intoxication, other (or unknown) substance withdrawal, other (or unknown) substance related disorder and gambling disorder; as well as to compounds of the invention of the formula I or of an N-oxide, a stereoisomer or of pharmaceutically acceptable salts thereof for the treatment and/or prophylaxis of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis; as well as to compounds of the invention of the formula I or of an N-oxide, a stereoisomer or of pharmaceutically acceptable salts thereof for the treatment and/or prophylaxis of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain; as well as to compounds of the invention of the formula I or of an N-oxide, a stereoisomer or of pharmaceutically acceptable salts thereof for the treatment and/or prophylaxis of the above-listed disorders. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient in need thereof.

Concerning the definition of vasopressin-related diseases, reference is made to the above statements made in context with the use according to the invention. Thus, preferred embodiments of the method of the invention correspond to preferred embodiments of the use according to the invention.

The patient to be treated prophylactically or therapeutically with the method of the invention is preferably a mammal, for example a human or a nonhuman mammal or a nonhuman transgenic mammal. Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, stereoisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis scheme 1, are explained in greater detail merely by way of example using the given examples without being exclusively restricted to synthesis route 1 or analogous methods.

EXPERIMENTAL SECTION

Abbreviations Used:

ACN for acetonitrile; BOC for 1,1-dimethylethoxycarbonyl; DCM for dichloromethane; DEA for diethylamine; DIPEA for diisopropylethyl amine; DMF for dimethylformamide; DMSO for dimethyl sulfoxide; EtOAc for ethyl acetate; EtOH for ethanol; IPA for isopropanol; MeOH for methanol; MeOD for deuteromethanol; MTBE for methyl tert-butyl ether; PE for petrol ether; TFA for trifluoroacetic acid; THF for tetrahydrofuran; rt for room temperature (20-25° C.); OEt for ethoxy; OMe for methoxy; RT for retention time; h or hrs for hour(s); min for minute(s); d for day(s); aq. for aqueous; conc. for concentrated; eq. for equivalent(s); quant. for quantitative; RP for reversed phase; TLC for thin layer chromatography; p for pseudo (for example pt pseudo triplet); b for broad (for example bs broad singlet); s for singlet; d for doublet; t for triplet; m for multiplet; dd for doublet of doublets; dt for doublet of triplets; tt for triplet of triplets.

LC-MS was recorded on Agilent 1200 HPLC/6110 SQ system by the following conditions:
Method A:
Method Info: Mobile Phase: A: Water (0.05% TFA) B: ACN (0.05% TFA)
Gradient: 5% B for 0.1 min, increase to 95% B within 0.7 min, 95% B for 0.9 min, back to 5% B within 0.01 min.
Flow Rate: 3.0 mL/min
Column: Zorbax SB-C18 Rapid Resolution HT, 4.6*30 mm, 1.8 μm
Column Temperature: 45° C.
Method B:
Method Info: Mobile Phase: A: Water (10 mM $NH_4HCO_3$) B: ACN
Gradient: 5% B for 0.2 min, increase to 95% B within 1.2 min,
95% B for 1.6 min, back to 5% B within 0.01 min.
Flow Rate: 1.8 mL/min
Column: XBridge C18, 4.6*50 mm, 3.5 μm
Column Temperature: 50° C.
Method C:
Method Info: Mobile Phase: A: Water (10 mM $NH_4HCO_3$) B: ACN
Gradient: 5% for 0.2 min, increase to 95% B within 1.7 min, 95% B for 1.4 min, back to 5% B within 0.01 min
Flow Rate: 2.1 mL/min
Column: XBridge C18, 4.6*50 mm, 3.5 μm
Column Temperature: 50° C.
Method D:
Method Info: Mobile Phase: A: Water (0.01% TFA) B: ACN (0.01% TFA)
Gradient: 5% B for 0.2 min, increase to 95% B within 1.7 min,
95% B for 1.3 min, back to 5% B within 0.01 min
Flow Rate: 2.3 mL/min
Column: XBridge C18, 4.6*50 mm, 3.5 μm
Column Temperature: 50° C.

All mass spectra were taken under electrospray ionisation (ESI) methods. Chiral-HPLC was recorded on column AD-H, AS-H, OJ-H, OD sepaxtel.

The starting materials used in the examples are either commercially available or can be synthesized by the average skilled person trained in organic chemistry following routine laboratory practice as outlined, for example in the examples below.

I. Preparation of Building Blocks a) Amines a1) 2-(1-Oxetan-3-yl-piperidin-4-yl)-2,6-diaza-spiro [3.3]heptane a1.1) 6-(1-Benzyl-piperidin-4-yl)-2,6-diaza-spiro [3.3]heptane-2-carboxylic acid tert-butyl ester 1-Benzylpiperidin-4-one (20.8 mmol, 3.9 g) and concentrated acetic acid (1.2 mL) were added to a solution of tert-butyl 2,6-diazaspiro[3.3]heptane-2-carboxylate oxalate (10.4 mmol, 3 g) in MeOH (100 mL). The solution was stirred for 1 h and NaCNBH$_3$ (12.5 mmol, 0.8 g) was added portionswise. The mixture was stirred over night at rt and poured onto cold 5% aq. K$_2$CO$_3$ (100 mL) and extracted three-times with ethyl acetate (100 mL), the organic phases were combined and washed with water three-times (100 mL) and dried on Na$_2$SO$_4$. It was filtered off, evaporated in vacuo and passed through a silicagel column (eluent: EtOAc: MeOH 1:1). Yield: 3.77 g (98%).

ESI-MS: [M+H$^+$]=372.2 a1.2) 6-Piperidin-4-yl-2,6-diaza-spiro[3.3]heptane-2-carboxylic acid tert-butyl ester tert-butyl 6-(1-benzylpiperidin-4-yl)-2,6-diazaspiro[3.3] heptane-2-carboxylate (4.0 mmol, 1.50 g) was dissolved in EtOH (100 mL) and hydrogenated in the presence of Pd/C. The mixture was further stirred overnight under H$_2$-atmosphere. The catalysator was filtered off, and the filtrate was evaporated in vacuo. Yield: 1.13 g (99%). The title compound was used in the next step without further purification a1.3) 6-(1-Oxetan-3-yl-piperidin-4-yl)-2,6-diaza-spiro[3.3]heptane-2-carboxylic acid tert-butyl ester Oxetan-3-one (1.78 mmol, 128 mg) and concentrated acetic acid (0.2 mL) were added to a solution of tert-butyl 6-(piperidin-4-yl)-2,6-diazaspiro[3.3]heptane-2-carboxylate (1.78 mmol, 500 mg) in EtOH (5 mL). The solution was stirred for 1 h and NaCNBH$_3$ (2.13 mmol, 134 mg) was added portionswise. The mixture was stirred over night at rt, poured onto cold 5% aq. K$_2$CO$_3$ (20 mL) and extracted three-times with ethyl acetate (20 mL). The organic phases were combined, washed with water (20 mL) three-times, dried on Na$_2$SO$_4$, filtered and evaporated in vacuo. It was passed through a silicagel column (eluent: CH$_2$Cl$_2$:2M NH$_3$/ EtOH 9:1. Yield: 296.2 mg (49%).

a1.4) 2-(1-Oxetan-3-yl-piperidin-4-yl)-2,6-diaza-spiro[3.3]heptane tert-butyl 6-(1-(oxetan-3-yl)piperidin-4-yl)-2,6-diazaspiro[3.3]heptane-2-carboxylate (0.86 mmol, 290 mg) was dissolved in CH$_2$Cl$_2$ (2 mL) and then treated with TFA (0.7 mL). The mixture was stirred at rt for 1 h. The solvent was evaporated under vacuo, and the residue treated with ether. The precipitate was filtered off, washed with ether, dried under vacuo and used in the next step without further purification. Yield: 368.3 mg (74%).

a2) 4-(2-(2,6-diazaspiro[3.3]heptan-2-yl)ethyl)morpholine a2.1) 6-(2-Morpholin-4-yl-ethyl)-2,6-diaza-spiro[3.3]heptane-2-carboxylic acid tert-butyl ester 2-Morpholinoacetaldehyde as NaHSO$_3$-salt (6.9 mmol, 1.6 g) and concentrated acetic acid (0.8 mL) were added to a solution of tert-butyl 2,6-diazaspiro[3.3]heptane-2-carboxylate oxalate (6.9 mmol, 2.0 g) in EtOH (100 mL). The mixture was stirred for 1 h, NaCNBH$_3$ (8.3 mmol, 0.5 g) was added portionswise, and further stirred over night at rt. The mixture was poured onto cold 5% aq. K$_2$CO$_3$ (100 mL) and extracted three-times with ethyl acetate (100 mL); the organic phases were combined, washed with water three-times (100 mL), dried on Na$_2$SO$_4$, filtered and evaporated in vacuo. The crude product was passed through a silicagel column (eluent: CH$_2$Cl$_2$:MeOH 9:1). Yield: 1.19 g (55%).

a2.2) 4-(2-(2,6-diazaspiro[3.3]heptan-2-yl)ethyl)morpholine tert-butyl 6-(2-morpholinoethyl)-2,6-diazaspiro[3.3]heptane-2-carboxylate (3.82 mmol, 1.2 g) was dissolved in CH$_2$Cl$_2$ (10 mL) and then treated with TFA (2.9 mL). The mixture was stirred at rt for 1 h. The solvent was removed under vacuo, the residue precipitated in ether; the solid was filtered off, washed with ether and dried under vacuo. Yield: 1.83 g (87%).

500 mg of the TFA-salt was passed through a column packed with Al$_2$O$_3$ neutral (eluent: CH$_2$Cl$_2$:2M NH$_3$/EtOH 17:3) to give 106.1 mg of the title compound.

a3) 6-(4-methylpiperazin-1-yl)-2-azaspiro[3.3]heptane tris(2,2,2-trifluoroacetate)

a3.1) tert-butyl 6-(4-methylpiperazin-1-yl)-2-azaspiro[3.3]heptane-2-carboxylate 1-Methylpiperazin (4.73 mmol, 0.47 g) and concentrated acetic acid (0.5 mL) were added to a solution of tert-butyl 6-oxo-2-azaspiro[3.3]heptane-2-carboxylate (4.73 mmol, 1.0 g) in EtOH (15 mL). It was stirred for 1 h and NaCNBH$_3$ (5.68 mmol, 0.36 g) was added portionswise, and the reaction mixture was further stirred over night at rt. The mixture was poured onto cold 5% aq. K$_2$CO$_3$ (15 mL) and extracted three-times with ethyl acetate (15 mL); the organic phases were combined, washed with water three-times (15 mL), dried on Na$_2$SO$_4$, filtered and evaporated in vacuo. It was passed through a silicagel column [eluent: 1.) EtOAc: MeOH 17:3 and 2.) CH$_2$Cl$_2$:MeOH 1:1]. Yield: 1.1 g (78%).

ESI-MS: [M+H$^+$]=296.2 a3.2) 6-(4-methylpiperazin-1-yl)-2-azaspiro[3.3] heptane tris(2,2,2-trifluoroacetate)

tert-butyl 6-(4-methylpiperazin-1-yl)-2-azaspiro[3.3]heptane-2-carboxylate (3.39 mmol, 1.0 g) was dissolved in CH$_2$Cl$_2$ and then treated with TFA (2.6 mL). The mixture was stirred at rt for 1 h. The solvent was evaporated under vacuo, the residue treated with ether; the precipitate was filtered off, washed with ether and dried under vacuo. Yield: 1.23 g (68%).

a4) 2-(1-isopropylpiperidin-4-yl)-2,6-diazaspiro[3.3] heptane tris(2,2,2-trifluoroacetate)

a4.1) tert-butyl 6-(1-isopropylpiperidin-4-yl)-2,6-diazaspiro[3.3]heptane-2-carboxylate The title compound was prepared in analogy to the method described in example a3.2)

a4.2) 2-(1-isopropylpiperidin-4-yl)-2,6-diazaspiro [3.3]heptane tris(2,2,2-trifluoroacetate)

tert-butyl 6-(1-isopropylpiperidin-4-yl)-2,6-diazaspiro [3.3]heptane-2-carboxylate (3.1 mmol, 1.0 g) was dissolved in CH$_2$Cl$_2$ (10 mL) and then treated with TFA (62 mmol, 7.1 g). The mixture was stirred at rt for 1 h and then evaporated under vacuo at rt. Yield: 1.67 g (96%).

a5) 2-(1-(2-methoxyethyl)piperidin-4-yl)-2,6-diazaspiro[3.3]heptane tris(2,2,2-trifluoroacetate)

a5.1) tert-butyl 6-(1-(2-methoxyethyl)piperidin-4-yl)-2,6-diazaspiro[3.3]heptane-2-carboxylate Cesium carbonate (1.78 mmol, 579 mg) and 1-chloro-2-methoxyethane (1.42 mmol, 134 mg) were added to a solution of tert-butyl 6-(piperidin-4-yl)-2,6-diazaspiro[3.3]heptane-2-carboxylate (0.71 mmol, 200 mg) in acetonitrile (10 mL). The reaction mixture was then refluxed for 12 h, and further stirred over night at room temperature. The reaction was monitored by TLC (eluent: 10% MeOH/$CH_2Cl_2$). The mixture was poured onto cold 5% aq. $K_2CO_3$ (10 mL) and extracted three-times with ethyl acetate (10 mL); the organic phases were combined, washed with water three-times (10 mL), dried on $Na_2SO_4$, filtered and evaporated in vacuo. The crude was passed on a silicagel column (eluent: 10-20% MeOH/$CH_2Cl_2$). Yield: 47 mg (20%) ESI-MS: [M+H$^+$]=340.30 a5.2) 2-(1-(2-methoxyethyl)piperidin-4-yl)-2,6-diazaspiro[3.3]heptane tris(2,2,2-trifluoroacetate)

The title compound was prepared in analogy to the method described in example a4.2) ESI-MS: [M+H$^+$]= 240.20 b) 2,3-dioxoindoline-6-carbonitrile b1.1) 2-Oxoindoline-6-carbonitrile

A mixture of palladium-tetrakis(triphenylphosphine) (10.90 g, 9.43 mmol), 6-bromoindolin-2-one (10 g, 47.2 mmol) and dicyanozinc (7.75 g, 66.0 mmol) in DMF (80 mL) was heated to 80° C. for 16 h. The reaction mixture was cooled to rt and water was added. The aqueous layer was extracted with ethyl acetate. The combined organic layers were washed with brine, dried over $Na_2SO_4$, filtered, and concentrated under reduced pressure. The crude material was purified by column chromatography (silica gel column and elution with 5% MeOH/$CH_2Cl_2$) to give 2-oxoindoline-6-carbonitrile (5.97 g, 37.7 mmol, 80% yield) as a brown solid.
RT=1.15 min (3 min).

b1.2) 2,3-dioxoindoline-6-carbonitrile

A mixture of 2-oxoindoline-6-carbonitrile (5 g, 31.6 m mol) and selenium dioxide (17.54 g, 158 mmol) in 1,4-dioxane (50 mL) was stirred at 100° C. for 1 h. LCMS indicated complete conversion to the product. The solution was deposited onto silica gel and loaded onto a silica gel column and eluted with 60% $CH_2Cl_2$/EtOAc. After evaporation, the title compound was obtained (1.023 g, 5.94 mmol, 18.8% yield).
RT=1.20 min (3 min).
$^1$H-NMR (DMSO, 400 MHz): 11.34 (s, 1H), 7.65~7.69 (m, 1H), 7.50~7.52 (m, 1H), 7.28 (s, 1H).

c) 3-hydroxy-2-oxoindoline-5-carbonitrile c1) 3-[2-(1,1-difluoroethyl)-3-pyridyl]-3-hydroxy-2-oxoindoline-5-carbonitrile c1.1) 1-(3-bromopyridin-2-yl)ethanone 3-bromopicolinonitrile (13.7 g, 74.9 mmol) was dissolved in THF (100 mL), stirred and cooled to about 0° C. Methyl magnesium iodide (49.9 ml, 150 mmol) was slowly added to the mixture. The resulting reaction was stirred at about 0° C. for about 2 h. LCMS indicated complete conversion to the product. The reaction mixture was poured onto ice cold water and the mixture was acidified with 1N HCl to pH 2 to 3. The aqueous layer was extracted with ethyl acetate (3×100 mL), dried over $Na_2SO_4$, filtered, and concentrated under reduced pressure. The crude product was purified by chromatography (silica gel column, elution with 5% EtOAc/PE to provide 1-(3-bromopyridin-2-yl)ethanone (10 g, 50 mmol, 66.8% yield) as a brown oil.
LCMS (Method D): m/z 201 (M+H); RT=1.51 min (3 min).
$^1$H-NMR (CDCl$_3$, 400 MHz): 8.57~8.59 (m, 1H), 7.98~8.01 (m, 1H), 7.29 (t, J=3.6 Hz, 1H), 2.69 (s, 3H).

c1.2) 3-bromo-2-(1,1-difluoroethyl)pyridine 1-(3-bromopyridin-2-yl)ethanone (7.2 g, 36.0 mmol) was dissolved in DCM (50 mL), stirred and then cooled to 0° C. Diethylaminosulfur trifluoride (38.0 ml, 288 mmol) was added dropwise via syringe to the solution. The resulting reaction was stirred at rt for about 3 days. TLC indicated partial conversion to the product with starting material remaining. The reaction mixture was carefully poured onto ice cold water. The aqueous layer was extracted with DCM (3×50 mL), dried over $Na_2SO_4$, filtered, and concentrated under reduced pressure. The crude product was purified by chromatography (silica gel column, elution with 20:1 PE/EtOAc) to give 3-bromo-2-(1,1-difluoroethyl)pyridine (3.60 g, 16.20 mmol, 45% yield).

c1.3) 3-(2-(1,1-difluoroethyl)pyridin-3-yl)-3-hydroxy-5-iodoindolin-2-one

To a stirred solution of 5-iodoindoline-2,3-dione (6 g, 21.98 mmol) in THF (50 mL), was added sodium hydride (1.011 g, 25.3 mmol). The resulting suspension was stirred at rt for 3 h. While isopropyl magnesium chloride (33.0 ml, 65.9 mmol) and triethylamine (9.19 mL, 65.9 mmol) were dissolved in THF (50 mL) and stirred and 3-bromo-2-(1,1-difluoroethyl)pyridine (7.32 g, 33.0 mmol) was added. The obtained Grignard solution was stirred for 3 h at 0° C. and then added to the ice-water cooled 5-iodoisatin sodium salt over 3 min. The reaction mixture was stirred at 0° C. for 2 hour. LCMS indicated partial conversion to the product with starting material remaining. The reaction was diluted with sat NH$_4$Cl. The combined aqueous layers were washed 3 times with ethyl acetate. The combined organic layers were dried over $Na_2SO_4$ and filtered through sintered glass funnel. The sample was deposited onto silica gel and loaded onto a silica gel column and eluted with 10:1 $CH_2Cl_2$/EtOAc to give the title compound (2.8 g, 5.52 mmol, 25.1% yield).
LCMS (Method B): m/z 417 (M+H); RT=1.63 min (3 min).
$^1$H-NMR (DMSO, 400 MHz): 10.51 (s, 1H), 8.65~8.67 (m, 2H), 7.68~7.71 (m, 1H), 7.54~7.57 (m, 1H), 7.07 (s, 1H), 7.02 (d, J=1.6 Hz, 1H), 6.72 (d, J=8.4 Hz, 1H), 1.72 (t, J=18.8 Hz, 3H).

c1.4) 3-[2-(1,1-difluoroethyl)-3-pyridyl]-3-hydroxy-2-oxo-indoline-5-carbonitrile A mixture of palladium-tetrakis(triphenylphosphine), (0.500 g, 0.433 mmol), 3-(2-(1,1-difluoroethyl)pyridin-3-yl)-3-hydroxy-5-iodoindolin-2-one (1.8 g, 4.33 mmol) and dicyanozinc (0.711 g, 6.06 mmol) in DMF (10 mL) was heated to 100° C. for 2 h under nitrogen. LCMS indicated complete conversion to the product. The reaction mixture was cooled to rt and water was added. The aqueous layer was extracted with ethyl acetate (3×50 mL). The combined organic layer was washed with brine, dried over $Na_2SO_4$, filtered, and concentrated under reduced pressure. The crude material was purified by column chromatography (silica gel column, elution with 5% MeOH/$CH_2Cl_2$) to give the title compound (1.212 g, 3.46 mmol, 80% yield).

LCMS (Method B): m/z 315 (M+H), RT: 1.46 min (3.0 min).

$^1$H-NMR (DMSO, 400 MHz): 10.91 (s, 1H), 8.66~8.71 (m, 2H), 7.70~7.73 (m, 2H), 7.23 (m, 2H), 7.00~7.02 (m, 1H), 1.73 (t, J=19.2 Hz, 3H).

d) 2-oxo-indoline-5-carbonitrile and separation of the enantiomers by preparative Supercritical Fluid Chromatography (SFC)

d1) (±)-3-(2,6-Diazaspiro[3.3]heptan-6-yl)-3-(2-ethoxy-5-methoxy-phenyl)-2-oxo-indoline-5-carbonitrile d1.1) 3-(2-Ethoxy-5-methoxy-phenyl)-3-hydroxy-2-oxo-2,3-dihydro-1H-indole-5-carbonitrile Preparation of the Grignard reagent: To a solution of Mg (16.4 g, 675 mmol) in THF (500 mL) was added $I_2$ (0.17 g, 0.675 mmol) and 2-bromo-1-ethoxy-4-methoxybenzene (31.2 g, 135 mmol). The mixture was heated to 80° C. for 2 hrs.

To a solution of 2,3-dioxoindoline-5-carbonitrile (23.2 g, 135 mmol) in THF (1000 mL) was added NaH (5.4 g, 135 mmol) at 0° C. The mixture was stirred at 0° C. for 2 hrs. To the resulting mixture was added the above-mentioned Grignard reagent (34.5 g, 135 mmol) dropwise at 25° C. Then the mixture was stirred at 80° C. for 3 hrs. The reaction was cooled to 25° C., slowly poured to cold saturated $NH_4Cl$ solution (half amount of THF) with stirring. The reaction mixture was extracted twice with ethyl acetate (same amount with THF). The combined organic phase was washed twice with brine and dried over $Na_2SO_4$ and concentrated under reduced pressure. The precipitate was collected by filtration and washed with cold EtOAc and MTBE. The residue solvent was removed under reduced pressure to give the title compound (yield 53%) as a pale yellow solid.

$^1$H NMR (400 MHz, MeOD): δ 7.63-7.60 (dd, J=8.4, 2.0 Hz, 1H), 7.54-7.53 (d, J=2.8 Hz, 1H), 7.17-7.16 (d, J=1.2 Hz, 1H), 7.03-7.01 (d, J=8.0 Hz, 1H), 6.84-6.83 (m, 1H), 6.77-6.75 (d, J=8.8 Hz, 1H), 3.83 (s, 3H), 3.79-3.63 (m, 2H), 1.04-1.01 (t, J=7.2 Hz, 3H).

d1.2) 3-Chloro-3-(2-ethoxy-5-methoxy-phenyl)-2-oxo-2,3-dihydro-1H-indole-5-carbonitrile To the solution 3-(2-ethoxy-5-methoxy-phenyl)-3-hydroxy-2-oxo-2,3-dihydro-1H-indole-5-carbonitrile (46 g, 142 mmol) in DCM (300 mL) was added pyridine (15.5 mL, 192 mmol), then the mixture was cooled to 0° C. and $SOCl_2$ (14.1 mL, 193 mmol) was added dropwise. The reaction mixture was stirred at 0° C. for 2 hrs, poured into water and extracted with DCM 3 times. The combined organic phase was washed with water 3 times, dried over $Na_2SO_4$, filtered and concentrated under reduced pressure to give the title compound (yield 86%) as a pale yellow solid which was used to do the next step directly without any further purification.

LCMS (ESI$^-$): m/z 341 (M−H)$^-$ RT: 2.322 min d1.3) 6-[5-Cyano-3-(2-ethoxy-5-methoxy-phenyl)-2-oxo-2,3-dihydro-1H-indol-3-yl]-2,6-diaza-spiro[3.3]heptane-2-carboxylic acid tert-butyl ester To the solution of tert-butyl 2,6-diazaspiro[3.3]heptane-2-carboxylate compound with 1,2-dihydroperoxyethyne (1:1) (14.2 g, 49.3 mmol) in DCM (600 mL) was added DIPEA (60.8 mL, 348 mmol) at room temperature. After stirring for 5 min, 3-chloro-3-(2-ethoxy-5-methoxy-phenyl)-2-oxo-2,3-dihydro-1H-indole-5-carbonitrile (25 g, 58.3 mmol) was added and the mixture was stirred at room temperature overnight. The reaction mixture was slowly poured into cold water with stirring. The mixture was extracted with DCM 3 times. The combined organic phase was washed with water 3 times and dried over $Na_2SO_4$, concentrated under reduced pressure to a residue. EtOAc was added to the residue and stirred for 30 min. The precipitate was collected by filtration and washed with cold EtOAc and MTBE. The solvent was removed under reduced pressure to give the title compound (25 g, yield 85%) as a white solid.

$^1$H NMR (400 MHz, CDCl$_3$): δ 8.39 (s, 1H), 7.51-7.49 (m, 1H), 7.39-7.38 (d, J=3.2 Hz, 1H), 7.17-7.16 (d, J=1.6 Hz, 1H), 6.92-6.90 (d, J=8.4 Hz, 1H), 6.78-6.77 (d, J=5.6 Hz, 1H), 6.70-6.67 (d, J=9.2 Hz, 1H), 4.00-3.98 (m, 2H), 3.83 (s, 3H), 3.81-3.68 (m, 3H), 3.34 (m, 2H), 1.41 (s, 9H), 1.09-1.06 (t, J=7.2 Hz, 3H).

d1.4) (±)-3-(2,6-diazaspiro[3.3]heptan-6-yl)-3-(2-ethoxy-5-methoxy-phenyl)-2-oxo-indoline-5-carbonitrile To the solution of 6-[5-cyano-3-(2-ethoxy-5-methoxyphenyl)-2-oxo-2,3-dihydro-1H-indol-3-yl]-2,6-diaza-spiro[3.3]heptane-2-carboxylic acid tert-butyl ester (21 g, 41.6 mmol) in DCM (400 mL) was added TFA (75 mL) dropwise at rt. The mixture was stirred at rt overnight and then concentrated under reduced pressure. The residue was dissolved in DCM (200 mL), slowly poured into cold saturated $K_2CO_3$ solution (200 mL) with stirring. The mixture was extracted with DCM 3 times. The combined organic phase was washed with brine 2 times and dried over $Na_2SO_4$, concentrated under reduced pressure to give the title compound (16 g, yield 95%) as a yellow solid.

Separation of the Enantiomers by SFC 49 g of 3-(2,6-Diazaspiro[3.3]hepan-6-yl)-3-(2-ethoxy-5-methoxy-phenyl)-2-oxo-indoline-5-carbonitrile were separated by SFC to give enantiomer A1 (14.13 g, purity 94.9%, ee %=95.5%) and enantiomer A2 (19.14 g, purity 92.8%, ee %=91.4%).

Preparative Separation Method
Instrument: Thar350 preparative SFC
Column: ChiralPak ID—10 μm, 300×50 mmI·D.
Mobile phase: A for $CO_2$ and B for IPA (0.1% $NH_3.H_2O$)
Gradient: B 40%
Flow rate: 200 mL/min
Back pressure: 100 bar
Column temperature: 38° C.
Wavelength: 280 nm
Cycle time: ~7.5 min
Sample preparation: Compound was dissolved in ethanol to ~49 mg/mL
Injection: 8.0 ml per injection.
Analytical Separation Method:
Instrument: Thar analytical SFC Column: WHELK-O1(R,R), 250×4.6 mm, 5μ
Mobile phase: A for $CO_2$ and B for Isopropanol (0.05% DEA)
Gradient: B 40%
Flow rate: 2.4 mL/min
Back pressure: 100 bar
Column temperature: 35° C.
Wavelength: 220 nm Enantiomer A1

(+)-3-(2,6-diazaspiro[3.3]heptan-6-yl)-3-(2-ethoxy-5-methoxy-phenyl)-2-oxo-indoline-5-carbonitrile $^1$H NMR (400 MHz, MeOD): δ 7.61-7.59 (m, 1H), 7.39-7.38 (d, J=4.0 Hz, 1H), 7.10 (d, J=1.2 Hz, 1H), 7.03-7.01 (m, 1H), 6.84-6.77 (m, 2H), 3.82 (s, 3H), 3.72 (m, 3H), 3.62-3.59 (m, 2H), 3.37-3.35 (m, 2H), 1.11-1.07 (t, J=7.2 Hz, 3H).
LCMS (ESI+): m/z 405 (M+H)$^+$, RT: 1.740 min.
α (20° C., c=2.1 mg/mL, MeOH, l=1 dm): +147.80°;

Enantiomer A2

(−)-3-(2,6-diazaspiro[3.3]heptan-6-yl)-3-(2-ethoxy-5-methoxy-phenyl)-2-oxo-indoline-5-carbonitrile $^1$H NMR (400 MHz, MeOD): δ 7.61-7.59 (m, 1H), 7.39-7.38 (d, J=5.6 Hz, 1H), 7.10 (d, J=1.2 Hz, 1H), 7.03-7.01 (m, 1H), 6.84-6.77 (m, 2H), 3.82 (s, 3H), 3.72 (m, 3H), 3.62-3.59 (m, 2H), 3.37-3.35 (m, 2H), 1.11-1.07 (t, J=7.2 Hz, 3H).
LCMS (ESI+): m/z 405 (M+H)+, RT: 1.765 min
α (20° C., c=2.4 mg/mL, MeOH, l=1 dm): −123.32° d2) (±)-3-(2-Ethoxy-5-methoxy-phenyl)-3-[6-(1-methyl-piperidin-4-yl)-2,6-diazaspiro[3.3]hept-2-yl]-2-oxo-2,3-dihydro-1H-indole-5-carbonitrile To the solution of 3-(2,6-diaza-spiro[3.3]hept-2-yl)-3-(2-ethoxy-5-methoxy-phenyl)-2-oxo-2,3-dihydro-1H-indole-5-carbonitrile (15 g, 37.1 mmol) in MeOH (200 mL) was added 1-methylpiperidin-4-one (12.6 g, 111 mmol), acetic acid (11 g, 182 mmol) at rt. After stirring for 1 hr, $NaBH_3CN$ (11.6 g, 185 mmol) was added portionwise. The mixture was stirred at room temperature overnight and then poured into cold saturated $K_2CO_3$ solution (100 mL) slowly with stirring. The mixture was extracted with DCM 3 times. The combined organic phase was washed with brine 2 times and dried over $Na_2SO_4$, concentrated under reduced pressure to give a residue, which was dissolved in ethyl acetate (20 mL), and MTBE was added with stirring. The precipitate was collected by filtration and washed with cold ethyl acetate and MTBE. The residue solvent was removed under reduced pressure to give the title compound (yield 91%) as a white solid. 37 g of the title compound were separated by SFC to give enantiomer B1 (15.33 g, purity 95.6%, ee %=99.1%) and enantiomer B2 (15.14 g, purity 97.7%, ee %=97.5%).

Enantiomer B1

(−)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile $^1$H NMR (400 MHz, MeOD): δ 7.61-7.59 (m, 1H), 7.39-7.38 (d, J=3.2 Hz, 1H), 7.09 (s, 1H), 7.03-7.01 (d, J=7.6 Hz, 1H), 6.83-6.77 (m, 2H), 3.82 (s, 3H), 3.77-3.68 (m, 2H), 3.60-3.50 (m, 2H), 3.34-3.30 (m, 6H), 2.84-2.81 (m, 2H), 2.23 (s, 1H), 2.03-1.99 (m, 3H), 1.73-1.70 (m, 2H), 1.30-1.25 (m, 2H), 1.10-1.09 (t, J=7.2 Hz, 3H).
LCMS (ESI+): m/z 502 (M+H)$^+$, RT: 1.554 min.
α (20° C., c=2.3 mg/mL, MeOH, l=1 dm): −143.96°.

Enantiomer B2

(+)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile $^1$H NMR (400 MHz, MeOD): δ 7.61-7.59 (m, 1H), 7.39-7.38 (d, J=3.2 Hz, 1H), 7.09 (s, 1H), 7.03-7.01 (d, J=7.6 Hz, 1H), 6.83-6.77 (m, 2H), 3.82 (s, 3H), 3.77-3.68 (m, 2H), 3.60-3.50 (m, 2H), 3.34-3.30 (m, 6H), 2.84-2.81 (m, 2H), 2.23 (s, 1H), 2.03-1.99 (m, 3H), 1.73-1.70 (m, 2H), 1.30-1.25 (m, 2H), 1.10-1.09 (t, J=7.2 Hz, 3H).
LCMS (ESI+): m/z 502 (M+H)$^+$, RT: 1.617 min.
α (20° C., c=1.5 mg/mL, MeOH, l=1 dm): +141.92°.

II) Preparation of Compounds of Formula I

The compounds of formula I were prepared in analogy to the methods described in WO 2008/025735 and WO 2008/10739 and in the schemes described above. For example, the 2-oxo-indoline-compound in question was converted into the compound of the formula I by treatment with sulfonyl halide after deprotonation with a strong base.

Example 1

(±)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=5-methoxy-2-pyridyl, $R^6$=$OC_2H_5$, $R^{7a}$=$OCH_3$, $R^{7b}$=H and $X^6$=CH)
ESI-MS: [M+H$^+$]=673.2

Enantiomer 1A (+)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile The title compound was prepared from corresponding chiral precursor, (+)-3-(2,6-diazaspiro[3.3]heptan-6-yl)-3-(2-ethoxy-5-methoxy-phenyl)-2-oxo-indoline-5-carbonitrile (enantiomer A1 from example d1).
ESI-MS: [M+H$^+$]=673.3
α (20° C., c=1.1 mg/mL, MeOH, l=1 dm): +56.38°.

Enantiomer 1B (−)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile The title compound was prepared from corresponding chiral precursor, (−)-3-(2,6-diazaspiro[3.3]heptan-6-yl)-3-

(2-ethoxy-5-methoxy-phenyl)-2-oxo-indoline-5-carbonitrile (enantiomer A2 from example d1).

ESI-MS: [M+H$^+$]=673.30

α (20° C., c=1.7 mg/mL, MeOH, 1=1 dm): −115.38°.

Example 2

(±)-1-(2,4-dimethoxyphenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=2,4-dimethoxyphenyl, R$^6$=OC$_2$H$_5$, R$^{7a}$=OCH$_3$, R$^{7b}$=H and X$^6$=CH)

ESI-MS: [M+H$^+$]=702.30

Example 3

(±)-3-(2-ethoxy-5-methoxy-phenyl)-3-[2-(1-methyl-4-piperidyl)-2,6-diazaspiro[3.3]heptan-6-yl]-2-oxo-1-(8-quinolylsulfonyl)indoline-5-carbonitrile (Compound of formula I.1, where R$^1$=CN, R$^2$=H, B=8-quinolyl, R$^6$=OC$_2$H$_5$, R$^{7a}$=OCH$_3$, R$^{7b}$=H and X$^6$=CH)

ESI-MS: [M+H$^+$]=693.30

Example 4

(±)-3-(2-ethoxy-5-methoxy-phenyl)-1-(2-methoxy-phenyl)sulfonyl-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=2-methoxyphenyl, R$^6$=OC$_2$H$_5$, R$^{7a}$=OCH$_3$, R$^{7b}$=H and X$^6$=CH)

ESI-MS: [M+H$^+$]=672.30

Example 5

(±)-3-(2-ethoxy-5-methoxy-phenyl)-1-(4-methoxy-phenyl)sulfonyl-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=4-methoxyphenyl, R$^6$=OC$_2$H$_5$, R$^{7a}$=OCH$_3$, R$^{7b}$=H and X$^6$=CH)

ESI-MS: [M+H$^+$]=672.30

Example 6

(−)-3-(2-ethoxy-5-methoxy-phenyl)-1-(4-methoxy-phenyl)sulfonyl-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=4-methoxyphenyl, R$^6$=OC$_2$H$_5$, R$^{7a}$=OCH$_3$, R$^{7b}$=H and X$^6$=CH)

The title compound was prepared in analogy to the method described in Example 5 but starting from the chiral 3-(2-ethoxy-5-methoxy-phenyl)-3-[2-(1-methyl-4-piperidyl)-2,6-diazaspiro[3.3]heptan-6-yl]-2-oxo-indoline-5-carbonitrile ESI-MS: [M+H$^+$]=672.3

Example 7

(±)-3-(2-ethoxy-4-fluoro-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=5-methoxy-2-pyridyl, R$^6$=OC$_2$H$_5$, R$^{7a}$=H, R$^{7b}$=F and X$^6$=CH)

7.1 (±)-3-(2-Ethoxy-4-fluoro-phenyl)-3-[6-(1-methyl-piperidin-4-yl)-2,6-diaza-spiro[3.3]hept-2-yl]-2-oxo-2,3-dihydro-1H-indole-5-carbonitrile DIPEA (2.5 eq., 1.51 mmol, 0.26 mL) was added to a suspension of 2-(1-methylpiperidin-4-yl)-2,6-diazaspiro[3.3]heptane trihydrochloride (0.61 mmol, 184 mg) in CH$_2$Cl$_2$ (7 mL). It was stirred for 5 min until it became a clear solution. Then 3-chloro-3-(2-ethoxy-4-fluorophenyl)-2-oxoindoline-5-carbonitrile (0.61 mmol, 200 mg) was added and the mixture was stirred at rt over night. The mixture was poured into cold 5% aq. K$_2$CO$_3$ (20 mL) and extracted three-times with CH$_2$Cl$_2$ (20 mL), the organic phases were combined and washed with water (20 mL) three-times and dried on Na$_2$SO$_4$, filtered and evaporated. It was passed through a column chromatographie (packed with Al$_2$O$_3$ neutral, eluent: EtOAc:MeOH 9:1). Yield: 226.8 mg (77%).

ESI-MS: [M+H$^+$]=490.3;

7.2 (±)-3-(2-ethoxy-4-fluoro-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H$^+$]=661.2

Example 8

(±)-3-(2-ethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=5-methoxy-2-pyridyl, R$^6$=OC$_2$H$_5$, R$^{7a}$=H, R$^{7b}$=H and X$^6$=CH)

8.1 (±)-3-(2-Ethoxy-phenyl)-3-[6-(1-methyl-piperidin-4-yl)-2,6-diaza-spiro[3.3]hept-2-yl]-2-oxo-2,3-dihydro-1H-indole-5-carbonitrile

ESI-MS: [M+H+]=472.2.

8.2 (±)-3-(2-ethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H+]=643.3

Example 9

(±)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=5-methoxy-2-pyridyl, $R^6$=OC$_2$H$_5$, $R^{7a}$=H, $R^{7b}$=H and $X^6$=N)

9.1 (±)-3-(2-Ethoxy-pyridin-3-yl)-3-[6-(1-methyl-piperidin-4-yl)-2,6-diaza-spiro[3.3]hept-2-yl]-2-oxo-2,3-dihydro-1H-indole-5-carbonitrile

ESI-MS: [M+K$^+$]=511.2; [M+H$^+$]=473.3;

9.2 (±)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H$^+$]=644.3

Enantiomer 9A (+)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile The title compound was prepared from the corresponding chiral precursor (+)-3-(2-ethoxypyridin-3-yl)-3-(6-(1-methylpiperidin-4-yl)-2,6-diazaspiro[3.3]heptan-2-yl)-2-oxoindoline-5-carbonitrile (RT 2. 43 min) which was obtained by SFC separation from (±)-3-(2-ethoxypyridin-3-yl)-3-(6-(1-methylpiperidin-4-yl)-2,6-diazaspiro[3.3]heptan-2-yl)-2-oxoindoline-5-carbonitrile from Example 9.1.

Preparative separation method for (±)-3-(2-ethoxypyridin-3-yl)-3-(6-(1-methylpiperidin-4-yl)-2,6-diazaspiro[3.3]heptan-2-yl)-2-oxoindoline-5-carbonitrile
Instrument: Thar 80 preparative SFC
Column: ChiralPak AD-H, 250×30 mm I.D. 5 u
Mobile phase: A for CO$_2$ and B for 2-propanol (0.05% NH$_3$H$_2$O)
Gradient: B %=35%
Flow rate: 70 g/min
Back pressure: 100 bar
Column temperature: 40° C.
Wavelength: 220 nm
Cycle time: 8 min
Sample preparation: Racemic material was dissolved in methanol to 50 mg/mL and filtrated through membrane.
Injection: 1.2 mL per injection.
Work up: After separation, the fractions were dried off via rotary evaporator at bath temperature 35° C. to get the two enantiomers.

(±)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile ESI-MS: [M+H$^+$]=644.20
α (20° C., c=1.8 mg/mL, MeOH, l=1 dm): +112.54°;

Example 10

(±)-3-(2-ethoxy-5-methoxy-phenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile (Compound of formula I.3, where $R^1$=CN, $R^2$=H, B=5-methoxy-2-pyridyl, $R^6$=OC$_2$H$_5$, $R^{7a}$=OCH$_3$, $R^{7b}$=H and $X^6$=CH)

10.1 (±)-3-(2-Ethoxy-5-methoxy-phenyl)-3-[6-(1-oxetan-3-yl-piperidin-4-yl)-2,6-diaza-spiro[3.3]hept-2-yl]-2-oxo-2,3-dihydro-1H-indole-5-carbonitrile DIPEA (0.44 mmol, 0.08 mL) was added to a suspension of 2-(1-(oxetan-3-yl)piperidin-4-yl)-2,6-diazaspiro[3.3]heptane tris(2,2,2-trifluoroacetate) (0.44 mmol, 254 mg) in CH$_2$Cl$_2$ (7.5 mL). It was stirred for 5 min until it became a clear solution. Then 3-chloro-3-(2-ethoxy-5-methoxyphenyl)-2-oxoindoline-5-carbonitrile (0.44 mmol, 150 mg) was added and the mixture was stirred at rt over night. The mixture was poured into cold 5% aq. K$_2$CO$_3$ (20 mL) and extracted three-times with CH$_2$Cl$_2$ (20 mL), the organic phases were combined and washed with water (20 mL) three-times and dried on Na$_2$SO$_4$, filtered and evaporated. The residue was triturated in ether; the precipitate was filtered off and dried under vacuo. Yield: 207.7 mg (87%).
ESI-MS: [M+H$^+$]=544.3; [M+H$^+$—CN]=519.3;

10.2 (±)-3-(2-ethoxy-5-methoxy-phenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile

ESI-MS: [M+H$^+$]=715.3

Example 11

(+)-3-(2-ethoxy-5-methoxyphenyl)-1-((5-methoxy-pyridin-2-yl)sulfonyl)-3-(6-(1-(oxetan-3-yl)piperidin-4-yl)-2,6-diazaspiro[3.3]heptan-2-yl)-2-oxoindoline-5-carbonitrile (Compound of formula I.3, where $R^1$=CN, $R^2$=H, B=5-methoxy-2-pyridyl, $R^6$=OC$_2$H$_5$, $R^{7a}$=OCH$_3$, $R^{7b}$=H and $X^6$=CH)

11.1 (+)-tert-butyl 4-(6-(5-cyano-3-(2-ethoxy-5-methoxyphenyl)-2-oxoindolin-3-yl)-2,6-diazaspiro[3.3]heptan-2-yl)piperidine-1-carboxylate (+)-3-(2-ethoxy-5-methoxyphenyl)-2-oxo-3-(2,6-diazaspiro[3.3]heptan-2-yl)indoline-5-carbonitrile from Example d1) (Enantiomer A1; 1.24 mmol, 500 mg) was dissolved in EtOH (20 mL), 1-BOC-piperidin-4-one (1.36 mmol, 271 mg) and concentrated acetic acid (0.14 mL) were added. The solution was stirred for 1 h and NaCNBH$_3$ (1.48 mmol, 93 mg) was added portionswise, and further stirred over night at rt. The mixture was poured onto cold 5% aq. K$_2$CO$_3$ (20 mL) and extracted three-times with ethyl acetate (20 mL); the organic phases were combined, washed with water three-times (20 mL), dried on Na$_2$SO$_4$, filtered and evaporated in vacuo. It was passed through a silicagel column (eluent: EtOAc:MeOH 9:1). Yield: 552.2 mg (76%).
ESI-MS: [M+H$^+$]=588.3; 532.2 (-isobutene)

11.2 (+)-3-(2-ethoxy-5-methoxyphenyl)-2-oxo-3-(6-(piperidin-4-yl)-2,6-diazaspiro[3.3]heptan-2-yl)indoline-5-carbonitrile tris(2,2,2-trifluoroacetate)

(+)-tert-butyl 4-(6-(5-cyano-3-(2-ethoxy-5-methoxyphenyl)-2-oxoindolin-3-yl)-2,6-diazaspiro[3.3]heptan-2-yl)piperidine-1-carboxylate (0.9 mmol, 550 mg) was dissolved in $CH_2Cl_2$ (50 mL) and then treated with TFA (0.7 mL). The mixture was stirred at rt for 1 h. The solvent was removed under vacuo, and the residue triturated with MeOH. After 1 h at rt, the precipitate was filtered off, washed with ether and dried under vacuo.
Yield: 592.8 mg (76%).
ESI-MS: $[M+H^+]$=488.2

11.3 (+)-3-(2-ethoxy-5-methoxyphenyl)-3-(6-(1-(oxetan-3-yl)piperidin-4-yl)-2,6-diazaspiro[3.3]heptan-2-yl)-2-oxoindoline-5-carbonitrile (+)-3-(2-ethoxy-5-methoxyphenyl)-2-oxo-3-(6-(piperidin-4-yl)-2,6-diazaspiro[3.3]heptan-2-yl)indoline-5-carbonitrile tris(2,2,2-trifluoroacetate) (0.36 mmol, 300 mg), sodium acetate (1.1 mmol, 89 mg) were dissolved in EtOH (25 mL) and stirred for 15 min; oxetan-3-one (0.72 mmol, 52 mg) and concentrated acetic acid (0.02 mL) were added. The mixture was stirred for 1 h and $NaCNBH_3$ (0.43 mg, 27 mg) was added portionswise. It was further stirred over night at rt. The mixture was poured onto cold 5% aq. $K_2CO_3$ (25 mL) and extracted three-times with ethyl acetate (25 mL); the organic phases were combined, washed with water three-times (25 mL), dried with $Na_2SO_4$, filtered and evaporated in vacuo. It was passed through a silicagel column (eluent: $CH_2CL_2$:2M $NH_3$/EtOH 17:3). Yield: 158.3 mg (81%).
ESI-MS: $[M+H^+]$=544.3

11.4 (+)-3-(2-ethoxy-5-methoxyphenyl)-1-((5-methoxypyridin-2-yl)sulfonyl)-3-(6-(1-(oxetan-3-yl)piperidin-4-yl)-2,6-diazaspiro[3.3]heptan-2-yl)-2-oxoindoline-5-carbonitrile

ESI-MS: $[M+H^+]$=715.3

Example 12

(±)-3-(2-ethoxy-3-pyridyl)-1-(4-methoxyphenyl)sulfonyl-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=4-methoxyphenyl, $R^6$=OC$_2$H$_5$, $R^{7a}$=H, $R^{7b}$=H and $X^6$=N)
ESI-MS: $[M+H^+]$=644.20

Example 13

(±)-3-(2-ethoxy-5-methoxy-phenyl)-1-[(5-methoxy-2-pyridyl)sulfonyl]-3-[2-(2-morpholinoethyl)-2,6-diazaspiro[3.3]heptan-6-yl]-2-oxo-indoline-5-carbonitrile (Compound of formula I.6, where $R^1$=CN, $R^2$=H, B=5-methoxy-2-pyridyl, $R^6$=OC$_2$H$_5$, $R^{7a}$=OCH$_3$, $R^{7b}$=H and $X^6$=CH)

13.1 (±)-3-(2-Ethoxy-5-methoxy-phenyl)-3-[6-(2-morpholin-4-yl-ethyl)-2,6-diaza-spiro[3.3]hept-2-yl]-2-oxo-2,3-dihydro-1H-indole-5-carbonitrile 4-(2-(2,6-diazaspiro[3.3]heptan-2-yl)ethyl)morpholine (0.29 mmol, 100 mg) was dissolved in $CH_2Cl_2$ (20 mL) and treated with DIPEA (1.6 mmol, 207 mg). The mixture was stirred for 5 min until it became a clear solution. Then 3-chloro-3-(2-ethoxy-5-methoxyphenyl)-2-oxoindoline-5-carbonitrile (0.29 mmol, 100 mg) was added and the mixture was stirred at room temperature over night. The reaction was monitored by TLC (eluent: 10% MeOH/$CH_2Cl_2$). The mixture was poured onto cold water (20 mL) and extracted three-times with $CH_2Cl_2$ (20 mL); the organic phases were combined, washed with water three-times (20 mL), dried on $Na_2SO_4$, filtered and evaporated in vacuo. Yield: 130 mg (86%).
ESI-MS: $[M+H^+]$=518.20

13.2 (±)-3-(2-ethoxy-5-methoxy-phenyl)-1-[(5-methoxy-2-pyridyl)sulfonyl]-3-[2-(2-morpholinoethyl)-2,6-diazaspiro[3.3]heptan-6-yl]-2-oxo-indoline-5-carbonitrile

ESI-MS: $[M+H^+]$=689.25

Example 14

(±)-1-(4-cyanophenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=4-cyanophenyl, $R^6$=OC$_2$H$_5$, $R^{7a}$=OCH$_3$, $R^{7b}$=H and $X^6$=CH)
ESI-MS: $[M+H^+]$=667.20

Example 15

(±)-3-(2-ethoxy-5-methoxy-phenyl)-3-[2-(1-methyl-4-piperidyl)-2,6-diazaspiro[3.3]heptan-6-yl]-2-oxo-1-(p-tolylsulfonyl)indoline-5-carbonitrile (Compound of formula I.1, where $R^1$=CN, $R^2$=H, B=4-methylphenyl, $R^6$=OC$_2$H$_5$, $R^{7a}$=OCH$_3$, $R^{7b}$=H and $X^6$=CH)
ESI-MS: $[M+H^+]$=656.25

Example 16

(±)-3-(2-ethoxy-5-methoxy-phenyl)-1-(4-fluorophenyl)sulfonyl-3-[2-(1-methyl-4-piperidyl)-2,6-diazaspiro[3.3]heptan-6-yl]-2-oxo-indoline-5-carbonitrile
(Compound of formula I.1, where $R^1$=CN, $R^2$=H, B=4-fluorophenyl, $R^6$=OC$_2$H$_5$, $R^{7a}$=OCH$_3$, $R^{7b}$=H and $X^6$=CH)
ESI-MS: $[M+H^+]$=660.20

Example 17

(±)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile (Compound of formula I.7, where $R^1$=CN, $R^2$=H, B=5-methoxy-2-pyridyl, $R^6$=OC$_2$H$_5$, $R^{7a}$=OCH$_3$, $R^{7b}$=H and $X^6$=CH)

17.1 (±)-3-(2-Ethoxy-5-methoxy-phenyl)-3-[6-(4-methyl-piperazin-1-yl)-2-azaspiro[3.3]hept-2-yl]-2-oxo-2,3-dihydro-1H-indole-5-carbonitrile 6-(4-methylpiperazin-1-yl)-2-azaspiro[3.3]heptane tris(2,2,2-trifluoroacetate) (0.22 mol, 118 mg) was dissolved in CH$_2$Cl$_2$ (20 mL) and treated with DIPEA (1.20 mmol, 156 mg). It was stirred for 5 min until it became a clear solution. Then 3-chloro-3-(2-ethoxy-5-methoxyphenyl)-2-oxoindoline-5-carbonitrile (0.22 mmol, 75 mg) was added and the mixture was stirred at room temperature over night. The reaction was monitored by TLC (eluent: 10% MeOH/CH$_2$Cl$_2$). The mixture was passed through a pre-packed SiOH-Chromabond column (eluent: 3-10% MeOH/CH$_2$Cl$_2$). Yield: 91 mg (83%).

ESI-MS: [M+H$^+$]=502.20.

17.2 (±)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile

ESI-MS: [M+H$^+$]=673.30.

The title compound was obtained in form of two enantiomers. These enantiomers were separated via chiral chromatography, column DAICEL chiralpak IC 250×4.6 mm ID; Eluent 650 mL n-heptane/350 mL EtOH/1 mL TEA; flow 12 mL/min Enantiomer 17A (−)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile ESI-MS: [M+H$^+$]=673.30
RT 29.38 min Enantiomer 17B (+)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile ESI-MS: [M+H$^+$]=673.30.
RT 32.41 min Example 18

(±)3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=5-methoxy-2-pyridyl, R$^6$=OCH$_3$, R$^{7a}$=H, R$^{7b}$=H and X$^6$=CH)

18.1 (±)-3-(2-methoxyphenyl)-3-(6-(1-methylpiperidin-4-yl)-2,6-diazaspiro[3.3]heptan-2-yl)-2-oxoindoline-5-carbonitrile 2-(1-Methylpiperidin-4-yl)-2,6-diazaspiro[3.3]heptane trihydrochloride (0.25 mol, 76 mg) was dissolved in CH$_2$Cl$_2$ (20 mL) and treated with DIPEA (1.38 mmol, 178 mg). The mixture was stirred for 5 min until it became a clear solution. Then 3-chloro-3-(2-methoxyphenyl)-2-oxoindoline-5-carbonitrile (0.25 mmol, 75 mg) was added and the mixture was stirred at rt over night. The reaction was monitored by TLC (eluent: 10% MeOH/CH$_2$Cl$_2$). The mixture was poured onto cold water (20 mL) and extracted three-times with CH$_2$Cl$_2$ (20 mL); the organic phases were combined, washed with water three-times (20 mL), dried on Na$_2$SO$_4$, filtered and evaporated in vacuo. Yield: 104 mg (83%).

ESI-MS: [M+H$^+$]=458.20

18.2 (±)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H$^+$]=629.20.

The title compound was obtained in form of two enantiomers. These enantiomers were separated via chiral chromatography; column DAICEL chiralpak IC 250×4.6 mm ID; Eluent 500 mL n-heptan/500 mL CH$_2$Cl$_2$/20 mL EtOH/1 mL TEA; flow 12 mL/min Enantiomer 18A (+)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile The title compound was prepared from the corresponding chiral precursor (+)-3-(2-methoxyphenyl)-3-(6-(1-methylpiperidin-4-yl)-2,6-diazaspiro[3.3]heptan-2-yl)-2-oxoindoline-5-carbonitrile (RT 2. 42 min) which was obtained by SFC separation from (±)-3-(2-methoxyphenyl)-3-(6-(1-methylpiperidin-4-yl)-2,6-diazaspiro[3.3]heptan-2-yl)-2-oxoindoline-5-carbonitrile from Example 18.1.

SFC Preparative separation method for (±)-3-(2-methoxyphenyl)-3-(6-(1-methylpiperidin-4-yl)-2,6-diazaspiro[3.3]heptan-2-yl)-2-oxoindoline-5-carbonitrile
Instrument: Thar 80 preparative SFC
Column: ChiralPak AD-H, 250×30 mm I.D. 5 u
Mobile phase: A for CO$_2$ and B for ethanol (0.05% NH$_3$H$_2$O)
Gradient: B %=35%
Flow rate: 70 g/min
Back pressure: 100 bar
Column temperature: 40° C.
Wavelength: 220 nm
Cycle time: 7.5 min
Sample preparation: Racemic material was dissolved in methanol to 50 mg/mL and filtrated through membrane.
Injection: 1.0 mL per injection.
Work up: After separation, the fractions were dried off via rotary evaporator at bath temperature 35° C. to get the two enantiomers.

(+)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile α (20° C., c=1.7 mg/mL, MeOH, l=1 dm): +105.93°.
ESI-MS: [M+H$^+$]=629.20.

Example 19

(±)-3-(2-ethoxy-5-methoxy-phenyl)-3-[2-(1-isopropyl-4-piperidyl)-2,6-diazaspiro[3.3]heptan-6-yl]-1-[(5-methoxy-2-pyridyl)sulfonyl]-2-oxo-indoline-5-carbonitrile (Compound of formula I.2, where R$^1$=CN, R$^2$=H, B=5-methoxy-2-pyridyl, R$^6$=OC$_2$H$_5$, R$^{7a}$=OCH$_3$, R$^{7b}$=H and X$^6$=CH)

19.1 3-(2-ethoxy-5-methoxyphenyl)-3-(6-(1-isopropylpiperidin-4-yl)-2,6-diazaspiro[3.3]heptan-2-yl)-2-oxoindoline-5-carbonitrile The title compound was prepared in analogy to the method described in Example 18.1 ESI-MS: [M+H$^+$]= 530.30.

19.2 (±)-3-(2-ethoxy-5-methoxy-phenyl)-3-[2-(1-isopropyl-4-piperidyl)-2,6-diazaspiro[3.3]heptan-6-yl]-1-[(5-methoxy-2-pyridyl)sulfonyl]-2-oxo-indoline-5-carbonitrile

ESI-MS: [M+H$^+$]=701.30

Example 20

(±)-3-(2-ethoxy-5-methoxy-phenyl)-3-[2-[1-(2-methoxyethyl)-4-piperidyl]-2,6-diazaspiro[3.3]heptan-6-yl]-1-[(5-methoxy-2-pyridyl)sulfonyl]-2-oxo-indoline-5-carbonitrile (Compound of formula I.5, where $R^1$=CN, $R^2$=H, B=5-methoxy-2-pyridyl, $R^6$=OC$_2$H$_5$, $R^{7a}$=OCH$_3$, $R^{7b}$=H and $X^6$=CH)

20.1 3-(2-ethoxy-5-methoxyphenyl)-3-(6-(1-(2-methoxyethyl)piperidin-4-yl)-2,6-diazaspiro[3.3]heptan-2-yl)-2-oxoindoline-5-carbonitrile The title compound was prepared in analogy to the method described in Example 18.1.
ESI-MS: [M+H+]=546.30

20.2 (±)-3-(2-ethoxy-5-methoxy-phenyl)-3-[2-[1-(2-methoxyethyl)-4-piperidyl]-2,6-diazaspiro[3.3]heptan-6-yl]-1-[(5-methoxy-2-pyridyl)sulfonyl]-2-oxo-indoline-5-carbonitrile

ESI-MS: [M+H+]=717.30

Example 21

(±)-3-(2,5-dimethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=5-methoxy-2-pyridyl, $R^6$=OCH$_3$, $R^{7a}$=OCH$_3$, $R^{7b}$=H and $X^6$=CH)

21.1 3-(2,5-dimethoxyphenyl)-3-(6-(1-methylpiperidin-4-yl)-2,6-diazaspiro[3.3]heptan-2-yl)-2-oxoindoline-5-carbonitrile The title compound was prepared in analogy to the method described in Example 18.1.
ESI-MS: [M+H$^+$]=488.20.

21.2 (±)-3-(2,5-dimethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H$^+$]=659.30

Example 22

(±)-3-(2-methoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=5-methoxy-2-pyridyl, $R^6$=OCH$_3$, $R^{7a}$=H, $R^{7b}$=H and $X^6$=N)

22.1 3-(2-methoxypyridin-3-yl)-3-(6-(1-methylpiperidin-4-yl)-2,6-diazaspiro[3.3]heptan-2-yl)-2-oxoindoline-5-carbonitrile The title compound was prepared in analogy to the method described in Example 18.1 ESI-MS: [M+H$^+$]= 459.20.

22.2 (±)-3-(2-methoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile

ESI-MS: [M+H$^+$]=630.20.

Example 23

(+)-3-(2-methoxyphenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile (Compound of formula I.3, where $R^1$=CN, $R^2$=H, B=5-methoxy-2-pyridyl, $R^6$=OCH$_3$, $R^{7a}$=H, $R^{7b}$=H and $X^6$=CH)

23.1 3-(2-methoxyphenyl)-3-(6-(1-(oxetan-3-yl)piperidin-4-yl)-2,6-diazaspiro[3.3]heptan-2-yl)-2-oxoindoline-5-carbonitrile The title compound was prepared in analogy to the method described in Example 18.1.
ESI-MS: [M+H$^+$]=500.2.

23.2 (+)-3-(2-methoxyphenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile

ESI-MS: [M+H$^+$]=671.30.

Example 24

(+)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile (Compound of formula I.4, where $R^1$=CN, $R^2$=H, B=2,4-dimethoxyphenyl, $R^6$=OC$_2$H$_5$, $R^{7a}$=OCH$_3$, $R^{7b}$=H and $X^6$=CH)

24.1 (+)-3-(2-ethoxy-5-methoxyphenyl)-3-(6-(2-methylpyridin-4-yl)-2,6-diazaspiro[3.3]heptan-2-yl)-2-oxoindoline-5-carbonitrile DIPEA (0.49 mmol, 0.09 mL) was added to a suspension of (+)-3-(2,6-Diazaspiro[3.3]heptan-6-yl)-3-(2-ethoxy-5- methoxy-phenyl)-2-oxo-indoline-5-carbonitrile (enantiomer A1 from example d1; 0.49 mmol, 200 mg) and 4-chloro-2-methylpyridine (0.99 mol, 126 mg) in methanol (5 mL). The mixture was then stirred at 120° C. for 16 h. The reaction was monitored by TLC (eluent: 20% MeOH/CH$_2$Cl$_2$). The mixture was poured onto cold 5% aq. K$_2$CO$_3$ (5 mL) and extracted three-times with ethyl acetate (5 mL); the organic phases were combined, washed with water three-times (5 mL), dried on Na$_2$SO$_4$, filtered and evaporated in vacuo. Yield: 200 mg (82%).
ESI-MS:=[M+H$^+$]=496.20
α (20° C., c=1.7 mg/mL, MeOH, l=1 dm): +42.1°;

24.2 (+)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile

ESI-MS: [M+H$^+$]=696.20

Example 25

(+)-3-(2-ethoxy-5-methoxy-phenyl)-1-[(5-methoxy-2-pyridyl)sulfonyl]-3-[2-(2-methyl-4-pyridyl)-2,6-diazaspiro[3.3]heptan-6-yl]-2-oxo-indoline-5-carbonitrile (Compound of formula I.4, where R$^1$=CN, R$^2$=H, B=5-methoxy-2-pyridyl, R$^6$=OC$_2$H$_5$, R$^{7a}$=OCH$_3$, R$^{7b}$=H and X$^6$=CH) ESI-MS: [M+H$^+$]=667.20

Example 26

(±)-3-(2-methoxyphenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile (Compound of formula I.7, where R$^1$=CN, R$^2$=H, B=5-methoxy-2-pyridyl, R$^6$=OCH$_3$, R$^{7a}$=H, R$^{7b}$=H and X$^6$=CH)

26.1 (±)-3-(2-methoxyphenyl)-3-(6-(4-methylpiperazin-1-yl)-2-azaspiro[3.3]heptan-2-yl)-2-oxoindoline-5-carbonitrile The title compound was prepared in analogy to the method described in Example 18.1.
ESI-MS: [M+H$^+$]=459.20

26.2 (±)-3-(2-methoxyphenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile

ESI-MS: [M+H$^+$]=629.30

Example 27

(±)-3-(2-ethoxy-3-pyridyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile (Compound of formula I.7, where R$^1$=CN, R$^2$=H, B=5-methoxy-2-pyridyl, R$^6$=OC$_2$H$_5$, R$^{7a}$=H, R$^{7b}$=H and X$^6$=N)

27.1 (±)-3-(2-ethoxypyridin-3-yl)-3-(6-(4-methylpiperazin-1-yl)-2-azaspiro[3.3]heptan-2-yl)-2-oxoindoline-5-carbonitrile (T-2371)

The title compound was prepared in analogy to the method described in Example 18.1.
ESI-MS: [M+H$^+$]=473.25.

27.2 (±)-3-(2-ethoxy-3-pyridyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile

ESI-MS: [M+H$^+$]=644.20.

Example 28

(±)-3-(2-ethoxy-5-methoxy-phenyl)-1-[(5-methoxy-2-pyridyl)sulfonyl]-3-[2-[4-(oxetan-3-yl)piperazin-1-yl]-6-azaspiro[3.3]heptan-6-yl]-2-oxo-indoline-5-carbonitrile (Compound of formula I.9, where R$^1$=CN, R$^2$=H, B=5-methoxy-2-pyrdiyl, R$^6$=OC$_2$H$_5$, R$^{7a}$=OCH$_3$, R$^{7b}$=H and X$^6$=CH)

The title compound was prepared in analogy to the method described in Example 17.
ESI-MS: [M+H$^+$]=715.4; 478.2; 358.4; 238.2.

Example 29

(±)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-6-carbonitrile (Compound of formula I.1, where R$^1$=H, R$^2$=CN, B=5-methoxy-2-pyridyl, R$^6$=OC$_2$H$_5$, R$^{7a}$=OCH$_3$, R$^{7b}$=H and X$^6$=CH)

The title compound was prepared in analogy to the method described in Example 1 starting from 2,3-dioxoindoline-6-carbonitrile from Example b)
ESI-MS: [M+H$^+$]=673.2.

Example 30

(±)-3-[2-(1,1-difluoroethyl)-3-pyridyl]-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=5-methoxy-2-pyridyl, R$^6$=C(CH$_3$)F$_2$, R$^{7a}$=H, R$^{7b}$=H and X$^6$=N)

The title compound was prepared in analogy to the method described in Example 1 starting from 3-(2-(1,1-difluoroethyl)pyridin-3-yl)-3-hydroxy-2-oxoindoline-5-carbonitrile from Example c1;
ESI-MS: [M+H$^+$]=664.2;

Example 31

(3S)-3-(2-ethoxy-5-methoxy-phenyl)-1-[(6-methoxy-3-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where R$^1$=CN, R$^2$=H, B=6-methoxy-3-pyridyl, R$^6$=OC$_2$H$_5$, R$^{7a}$=OCH$_3$, R$^{7b}$=H and X$^6$=CH)

The title compound was prepared in analogy to the method described in Example 1 starting from (+)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile from Example d2, enantiomer B2.

ESI-MS: [M+H$^+$]=673.4; 337.2.

Example 32

(3S)-3-(2-ethoxy-5-methoxy-phenyl)-1-[(6-methoxy-2-pyridyl)sulfonyl]-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=6-methoxy-2-pyridyl, $R^6$=OC$_2$H$_5$, $R^{7a}$=OCH$_3$, $R^{7b}$=H and $X^6$=CH)

The title compound was prepared in analogy to the method described in Example 1 starting from (+)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile from Example d2, enantiomer B2.

ESI-MS: [M+H$^+$]=673.4; 337.2.

Example 33

(3S)-3-(2-ethoxy-5-methoxy-phenyl)-3-[2-(1-methyl-4-piperidyl)-2,6-diazaspiro[3.3]heptan-6-yl]-2-oxo-1-(2-pyridylsulfonyl)indoline-5-carbonitrile (Compound of formula I.1, where $R^1$=CN, $R^2$=H, B=2-pyridyl, $R^6$=OC$_2$H$_5$, $R^{7a}$=OCH$_3$, $R^{7b}$=H and $X^6$=CH)

The title compound was prepared in analogy to the method described in Example 1 starting from (+)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile from Example d2, enantiomer B2.

ESI-MS: [M+H$^+$]=643.3.

Example 34

(3S)-1-[(5-chloro-2-pyridyl)sulfonyl]-3-(2-ethoxy-5-methoxy-phenyl)-3-[2-(1-methyl-4-piperidyl)-2,6-diazaspiro[3.3]heptan-6-yl]-2-oxo-indoline-5-carbonitrile (Compound of formula I.1, where $R^1$=CN, $R^2$=H, B=5-chloro-2-pyridyl, $R^6$=OC$_2$H$_5$, $R^{7a}$=OCH$_3$, $R^{7b}$=H and $X^6$=CH)

The title compound was prepared in analogy to the method described in Example 1 starting from (+)-3-(2-ethoxy-5-methoxy-phenyl)-3-[2-(1-methyl-4-piperidyl)-2,6-diazaspiro[3.3]heptan-6-yl]-2-oxo-indoline-5-carbonitrile from Example d2, enantiomer B2.

ESI-MS: [M$^+$]=677.2; 339.2.

III. Determination of the Biological Activity

1. Vasopressin V1b Receptor Binding Assay:
Substances:

The test substances were dissolved in a concentration of 5 mM in 100% DMSO and further diluted to 5×10$^{-4}$ M to 5×10$^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (200 μl), membranes (26 g protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 μM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:
Substances:

The test substances were dissolved in a concentration of 5 mM M in DMSO. Further dilution of these DMSO solutions took place as described for V1b.

Membrane Preparation:

CHO-K1 cells with stably expressed human vasopressin Via receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (200 μl), membranes (40 μg protein in incubation buffer) from CHO-K1 cells with stably expressed human Via receptors (cell line hV1a_5_CHO) were incubated with 0.04 nM $^{125}$I-AVP (8-Arg-vasopressin, PerkinElmer NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 μM AVP (Fluka 94836). Duplicate determinations were carried out.

After incubation (60 minutes at room temperature), the samples were processed as described for V1b.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Membrane Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. Cell lysates were then centrifuged at 750×g at 4° C. for 20 minutes, the residue was taken up in incubation buffer (50 mM Tris, 10 mM MgCl$_2$, 0.1% BSA, pH 7.4), and aliquots corresponding to $10^7$ cells/ml were prepared. The aliquots were frozen at −80° C. until use.

Binding Assay:

On the day of the experiment, the cell lysate was thawed, homogenized, and diluted with incubation buffer (50 mM Tris, 10 mM MgCl$_2$, 0.1% BSA, pH 7.4) to the desired concentration. The reaction mixture of 0.200 ml was composed of cell lysate corresponding to $5\times10^4$ cells (HEK-293 cells expressing transiently human OT receptors) and 1 nM 3H-oxytocin (PerkinElmer NET858) in the presence of test substance (displacement experiment) or incubation buffer only (total binding). The nonspecific binding was determined in the presence of 1 μM oxytocin (Bachem AG, H2510). Determinations were carried out in duplicates. After 60 minutes incubation at room temperature, bound and free radioligand were separated by filtration under vacuum on GF/B UniFilter plates (Perkin Elmer #6005177) pre-incubated with 0.3% PEI. The bound radioactivity was determined by liquid scintillation measurement in a Microbeta (Perkin Elmer) plate counter.

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant human OT receptors was 7.6 nM and was used to calculate the Ki from competition binding experiments.

4. Determination of the Microsomal Half-Life:

The metabolic stability of the compounds of the invention was determined in the following assay.

The test substances were incubated in a concentration of 0.5 μM as follows:

0.5 μM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 μl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln2/T½/(content of microsomal protein in mg/ml)×1000 [ml/min/mg](modified from references: Di, The Society for Biomoleculur Screening, 2003, 453-462; Obach, D M D, 1999 vol 27. N 11, 1350-1359).

5. Methods for In Vitro Determination of the Cytochrome P450 (CYP) Inhibition

Luminescent Substrates for 2C9 and 3A4:

0.4 mg/ml human liver microsomes are preincubated with the test substances to be investigated (0-20 μM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 μM (or 50 μM) test substance in 50 mM potassium phosphate buffer for 5 min. The reaction is started with NADPH. After 30 min 4 μM midazolam (final concentration) are added, and incubation is continued for 10 min. 75 μl of the reaction solution are removed after 10 min, and stopped with 150 μl of acetonitrile solution.

Coincubation:

0.05 mg/ml microsomal protein (human liver microsomes) are preincubated with 4 μm midazolam (final concentration) and 0-10 μM (or 50 μM) test substance in 50 mM potassium phosphate buffer for 5 min. The reaction is started with NADPH. 75 μl of the reaction solution are removed after 10 min and stopped with 150 μl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in Mg/Ml)

The solubility in water of the compounds of the invention can be determined for example by the so-called shake flask method (as specified in *ASTM International: E* 1148-02, Standard test methods for measurement of aqueous solubility, Book of Standards Volume 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the Via receptor and a good metabolic stability, measured as microsomal clearance.

The results are listed in table B. The numbers of the compounds refer to the synthesis examples.

TABLE B

| Example | $K_i$(h-V1b)* [nM] | $K_i$(h-V1a)/ $K_i$(h-V1b) |
|---|---|---|
| 1 | ++ | +++ |
| 1A | +++ | +++ |
| 1B | + | +++ |
| 2 | + | ++ |
| 3 | + | +++ |
| 5 | ++ | + |
| 6 | + | — |
| 7 | ++ | +++ |
| 8 | ++ | +++ |
| 9 | ++ | +++ |
| 9A | +++ | +++ |
| 10 | ++ | +++ |
| 11 | +++ | +++ |
| 12 | + | + |
| 14 | + | +++ |
| 15 | + | ++ |
| 16 | + | ++ |
| 17 | +++ | +++ |
| 17B | +++ | +++ |
| 18 | +++ | +++ |
| 18A | +++ | + |
| 19 | +++ | +++ |
| 20 | ++ | +++ |
| 21 | +++ | + |
| 22 | ++ | + |
| 23 | ++ | + |
| 24 | + | +++ |
| 25 | +++ | +++ |
| 26 | ++ | ++ |
| 27 | ++ | +++ |
| 28 | ++ | +++ |
| 29 | ++ | — |
| 30 | ++ | + |
| 31 | ++ | + |
| 32 | + | — |
| 33 | ++ | +++ |
| 34 | +++ | +++ |

*h = human
Key:

| | $K_i$(h-V1b) | $K_i$(h-V1a)/ $K_i$(h-V1b) |
|---|---|---|
| + | >10-100 nM | 10-<25 |
| ++ | 1-10 nM | 25-75 |
| +++ | <1 nM | >75 |

The invention claimed is:
1. A compound of formula I

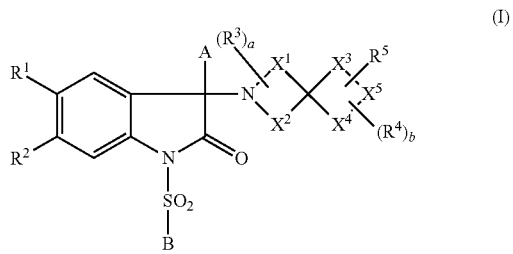

wherein
A is a ring selected from the group consisting of phenyl and 6-membered hetaryl containing 1 or 2 nitrogen atoms as ring members, where ring A carries one substituent $R^6$ and optionally one substituent $R^7$;
B is a ring selected from the group consisting of phenyl and a monocyclic or bicyclic heteroaromatic ring containing 1, 2 or 3 heteroatoms selected from the group consisting of O, N and S as ring members, where ring B may carry 1, 2 or 3 substituents $R^8$;
$X^1$, $X^2$, $X^3$ and $X^4$, independently of each other, are —$CH_2$— or —$CH_2CH_2$—;
$X^5$ is NH or $CH_2$;
$R^1$ is selected from the group consisting of hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;
$R^2$ is selected from the group consisting of hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;
$R^3$ and $R^4$, independently of each other and independently of each occurrence, are selected from the group consisting of hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy and $NR^9R^{10}$, and in case that $R^3$ or $R^4$ are bound to a carbon ring atom, are additionally selected from halogen; or two non-geminal radicals $R^3$ form together a group —$(CH_2)_k$—, where k is 1, 2, 3 or 4, where 1 or 2 hydrogen atoms in this group may be replaced by a methyl group; or two non-geminal radicals $R^4$ form together a group —$(CH_2)_k$—, where k is 1, 2, 3 or 4, where 1 or 2 hydrogen atoms in this group may be replaced by a methyl group; or two geminal radicals $R^3$ form together a group —$(CH_2)_j$—, where j is 2, 3, 4 or 5, where 1 or 2 hydrogen atoms in this group may be replaced by a methyl group; or two geminal radicals $R^4$ form together a group —$(CH_2)_j$—, where j is 2, 3, 4 or 5, where 1 or 2 hydrogen atoms in this group may be replaced by a methyl group; with the proviso that $R^3$ and $R^4$ are not halogen, hydroxyl, $C_1$-$C_4$-alkoxy or $C_1$-$C_4$-haloalkoxy if they are bound to a carbon atom in α-position to a nitrogen ring atom;
$R^5$ is selected from the group consisting of hydrogen, cyano, $C_1$-$C_6$-alkyl, $C_2$-$C_6$-alkenyl, $C_2$-$C_6$-alkynyl, $C_3$-$C_7$-cycloalkyl, where the four last-mentioned radicals may be partially or fully halogenated and/or may carry one or more substituents $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members; a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$; —$OR^{13}$; —$S(O)_lR^{13}$; $NR^{14}R^{15}$; and —$C(=O)R^{16}$;

$R^6$ and $R^7$, independently of each other, are selected from the group consisting of halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

each $R^8$ is independently selected from the group consisting of halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^9$ and $R^{10}$, independently of each other, are selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl;

each $R^{11}$ is independently selected from the group consisting of cyano, —$OR^{13}$, —$S(O)_lR^{13}$, $NR^{14}R^{15}$, —$C(=O)R^{16}$, $C_3$-$C_6$-cycloalkyl, $C_3$-$C_6$-halocycloalkyl, phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members, and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally $C_1$-$C_4$-alkyl or $C_1$-$C_4$-haloalkyl;

each $R^{12}$ is independently selected from the group consisting of halogen, hydroxyl, cyano, nitro, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-haloalkoxy-$C_1$-$C_4$-alkyl, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenyl, phenoxy, benzyloxy, where the phenyl moiety in the three last-mentioned radicals may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members, where the heteromonocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{13}$ is independently selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, phenyl which may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, where the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

$R^{14}$ and $R^{15}$, independently of each other and independently of each occurrence, are selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, phenyl which may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, where the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; $C_1$-$C_4$-alkylcarbonyl and $C_1$-$C_4$-haloalkylcarbonyl;

each $R^{16}$ is independently selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, phenyl, —$OR^{13}$ and $NR^{14}R^{15}$;

a is 0, 1 or 2;

b is 0, 1 or 2; and l is 0, 1 or 2;

or an N-oxide, stereoisomer or pharmaceutically acceptable salt thereof.

2. The compound as claimed in claim 1, wherein at least one hydrogen atom has been replaced by a deuterium atom.

3. The compound as claimed in claim 1, where $X^1$, $X^2$, $X^3$ and $X^4$ are —$CH_2$—.

4. The compound as claimed in claim 1, where $X^5$ is NH.

5. The compound as claimed in claim 1, where $R^5$ is bound to $X^5$.

6. The compound as claimed in claim 1, where A is phenyl or pyridyl, where A carries one substituent $R^6$ and optionally one substituent $R^7$.

7. The compound as claimed in claim 6, where A is phenyl or 3-pyridyl, where A carries the radical $R^6$ in 2-position and the radical $R^7$, if present, in 4- or 5-position, relative to the 1-position of the attachment point of A to the remainder of the molecule.

8. The compound as claimed in claim 1, where B is selected from the group consisting of phenyl, pyridyl and a 10-membered bicyclic heteroaromatic ring containing 1 or 2 nitrogen atoms as ring members, where B may carry 1, 2 or 3 substituents $R^8$.

9. The compound as claimed in claim 8, where B is selected from the group consisting of phenyl, pyridyl and quinolinyl, where B may carry 1, 2 or 3 substituents $R^8$.

10. The compound as claimed in claim 1, where $R^1$ is selected from the group consisting of hydrogen, halogen and cyano.

11. The compound as claimed in claim 10, where $R^1$ is selected from the group consisting of hydrogen, chlorine and cyano.

12. The compound as claimed in claim 1, where $R^2$ is selected from the group consisting of hydrogen, halogen and cyano.

13. The compound as claimed in claim 1, where $R^3$ and $R^4$, independently of each other and independently of each occurrence, are halogen or $C_1$-$C_4$-alkyl, with the proviso that $R^3$ and $R^4$ are not halogen if they are bound to a carbon atom in α-position to a nitrogen ring atom.

14. The compound as claimed in claim 1, where $R^3$ is selected from the group consisting of hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkyl which carries one substituent $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$.

15. The compound as claimed in claim 14, where $R^5$ is selected from the group consisting of $C_1$-$C_6$-alkyl which carries one substituent $R^{11}$; a 3-, 4-, 5- or 6-membered saturated heteromonocyclic ring containing 1 or 2 heteroatoms or heteroatom groups selected from the group consisting of O, N, S, NO, SO and $SO_2$ as ring members; and a 5- or 6-membered heteroaromatic ring containing 1 or 2 heteroatoms selected from O, N and S as ring members, where the saturated heteromonocyclic or the heteroaromatic ring may carry 1, 2 or 3 substituents $R^{12}$.

16. The compound as claimed in claim 15, where $R^5$ is selected from the group consisting of $C_1$-$C_4$-alkyl which carries one substituent $R^{11}$; a 6-membered saturated heteromonocyclic ring containing 1 or 2 heteroatoms selected from O and N as ring members; and a 6-membered heteroaromatic ring containing 1 or 2 nitrogen atoms as ring members, where the saturated heteromonocyclic or the heteroaromatic ring may carry 1 or 2 substituents $R^{12}$.

17. The compound as claimed in claim 1, where $R^{11}$ is selected from the group consisting of cyano; —$OR^{13}$; $NR^{14}R^{15}$; a 3-, 4-, 5-, 6- or 7-membered saturated heteromonocyclic ring containing 1, 2 or 3 heteroatoms or heteroatom groups selected from the group consisting of O, N, S, NO, SO and $SO_2$ as ring members; and a 5-, 6-, 7-, 8-, 9-, 10- or 11-membered saturated heterobicyclic ring containing 1, 2 or 3 heteroatoms or heteroatom groups selected from the group consisting of O, N, S, NO, SO and $SO_2$ as ring members, where the heteromoncyclic or heterobicyclic ring may carry 1, 2 or 3 substituents $R^{12}$; and as a substituent on a cycloalkyl ring, $R^{11}$ is additionally $C_1$-$C_4$-alkyl or $C_1$-$C_4$-haloalkyl.

18. The compound as claimed in claim 17, where $R^{11}$ is a 4-, 5- or 6-membered, saturated heteromonocyclic ring containing 1 or 2 heteroatoms or heteroatom groups selected from the group consisting of O, N, S, NO, SO and $SO_2$ as ring members, where the heteromoncyclic ring may carry 1 or 2 or 3 substituents $R^{12}$.

19. The compound as claimed in claim 1, where $R^{12}$ is selected from the group consisting of halogen, cyano, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkyl, fluorinated $C_1$-$C_4$-alkoxy-$C_1$-$C_4$-alkyl, phenyl which may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy; and a 3-, 4-, 5- or 6-membered saturated heteromonocyclic ring containing 1, 2 or 3 heteroatoms or heteroatom groups selected from the group consisting of O, N, S, NO, SO and $SO_2$ as ring members, where the heteromonocyclic ring may carry 1, 2 or 3 substituents selected from the group consisting of halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy.

20. The compound as claimed in claim 19, where $R^{12}$ is selected from the group consisting of $C_1$-$C_4$-alkyl, fluorinated $C_1$-$C_4$-alkyl, $C_1$-$C_4$-alkoxy-$C_1$-$C_4$-alkyl, fluorinated $C_1$-$C_4$-alkoxy-$C_1$-$C_4$-alkyl, and a 3-, 4-, 5- or 6-membered saturated heteromonocyclic ring containing 1 or 2 heteroatoms selected from the group consisting of O, N and S as ring members.

21. The compound as claimed in claim 1, where $R^6$ is selected from the group consisting of $C_1$-$C_3$-alkoxy, $C_1$-$C_3$-alkyl and fluorinated $C_1$-$C_3$-alkyl.

22. The compound as claimed in claim 1, where $R^7$ is halogen or $C_1$-$C_3$-alkoxy.

23. The compound as claimed in claim 1, where each $R^8$ is independently selected from the group consisting of halogen, cyano, $C_1$-$C_3$-alkyl, fluorinated $C_1$-$C_3$-alkyl, $C_1$-$C_3$-alkoxy and fluorinated $C_1$-$C_3$-alkoxy.

24. The compound as claimed in claim 23, where each $R^8$ is independently selected from the group consisting of fluorine, chlorine, cyano, methyl, methoxy and trifluoromethoxy.

25. The compound as claimed in claim 1, where a and b are independently 0 or 1.

26. The compound as claimed in claim 1, of formula IA

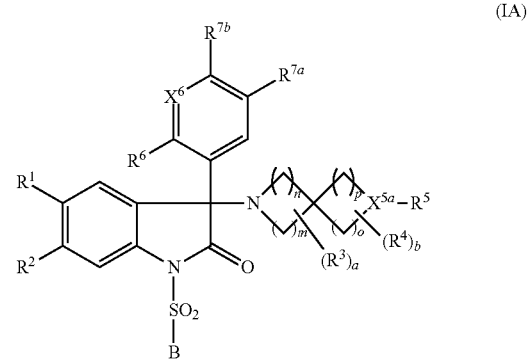

where
$X^{5a}$ is N or CH;
$X^6$ is N or CH;
$R^{7a}$ and $R^{7b}$, independently of each other, are hydrogen or have one of the definitions given for $R^7$, with the proviso that at least one of $R^{7a}$ and $R^{7b}$ is hydrogen;
m, n, o and p are independently of each other 1 or 2.

27. The compound as claimed in claim 26, where m, n, o and p are 1.

28. A compound selected from the group consisting of
(±)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;
(+)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;
(−)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-1-(2,4-dimethoxyphenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(+)-1-(2,4-dimethoxyphenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(−)-1-(2,4-dimethoxyphenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-3-[2-(1-methyl-4-piperidyl)-2,6-diazaspiro[3.3]heptan-6-yl]-2-oxo-1-(8-quinolylsulfonyl)indoline-5-carbonitrile;

(+)-3-(2-ethoxy-5-methoxy-phenyl)-3-[2-(1-methyl-4-piperidyl)-2,6-diazaspiro[3.3]heptan-6-yl]-2-oxo-1-(8-quinolylsulfonyl)indoline-5-carbonitrile;

(−)-3-(2-ethoxy-5-methoxy-phenyl)-3-[2-(1-methyl-4-piperidyl)-2,6-diazaspiro[3.3]heptan-6-yl]-2-oxo-1-(8-quinolylsulfonyl)indoline-5-carbonitrile;

(±)-3-(2-ethoxy-5-methoxy-phenyl)-1-(2-methoxyphenyl)sulfonyl-3-[2-(1-methyl-4-piperidyl)-2,6-diazaspiro[3.3]heptan-6-yl]-2-oxo-indoline-5-carbonitrile;

(+)-3-(2-ethoxy-5-methoxy-phenyl)-1-(2-methoxyphenyl)sulfonyl-3-[2-(1-methyl-4-piperidyl)-2,6-diazaspiro[3.3]heptan-6-yl]-2-oxo-indoline-5-carbonitrile;

(−)-3-(2-ethoxy-5-methoxy-phenyl)-1-(2-methoxyphenyl)sulfonyl-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(+)-3-(2-ethoxy-5-methoxy-phenyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(−)-3-(2-ethoxy-5-methoxy-phenyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(±)-3-(2-ethoxy-4-fluoro-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2-ethoxy-4-fluoro-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2-ethoxy-4-fluoro-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-S-carbonitrile;

(±)-3-(2-ethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2-ethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2-ethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2-ethoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile;

(+)-3-(2-ethoxy-5-methoxyphenyl)-1-((5-methoxypyridin-2-yl)sulfonyl)-3-(6-(1-(oxetan-3-yl)piperidin-4-yl)-2,6-diazaspiro[3.3]heptan-2-yl)-2-oxoindoline-5-carbonitrile;

(−)-3-(2-ethoxy-5-methoxyphenyl)-1-((5-methoxypyridin-2-yl)sulfonyl)-3-(6-(1-(oxetan-3-yl)piperidin-4-yl)-2,6-diazaspiro[3.3]heptan-2-yl)-2-oxoindoline-5-carbonitrile;

(±)-3-(2-ethoxy-3-pyridyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(+)-3-(2-ethoxy-3-pyridyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(−)-3-(2-ethoxy-3-pyridyl)-1-(4-methoxyphenyl)sulfonyl-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-(2-morpholinoethyl)-2,6-diazaspiro[3.3]heptan-6-yl]-2-oxo-indoline-5-carbonitrile;

(+)-3-(2-ethoxy-5-methoxy-phenyl)-1-[(5-methoxy-2-pyridyl)sulfonyl]-3-[2-(2-morpholinoethyl)-2,6-diazaspiro[3.3]heptan-6-yl]-2-oxo-indoline-5-carbonitrile;

(−)-3-(2-ethoxy-5-methoxy-phenyl)-1-[(5-methoxy-2-pyridyl)sulfonyl]-3-[2-(2-morpholinoethyl)-2,6-diazaspiro[3.3]heptan-6-yl]-2-oxo-indoline-5-carbonitrile;

(±)-1-(4-cyanophenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(+)-1-(4-cyanophenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(−)-1-(4-cyanophenyl)sulfonyl-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-3-[2-(1-methyl-4-piperidyl)-2,6-diazaspiro[3.3]heptan-6-yl]-2-oxo-1-(p-tolylsulfonyl)indoline-5-carbonitrile;

(+)-3-(2-ethoxy-5-methoxy-phenyl)-3-[2-(1-methyl-4-piperidyl)-2,6-diazaspiro[3.3]heptan-6-yl]-2-oxo-1-(p-tolylsulfonyl)indoline-5-carbonitrile;

(−)-3-(2-ethoxy-5-methoxy-phenyl)-3-[2-(1-methyl-4-piperidyl)-2,6-diazaspiro[3.3]heptan-6-yl]-2-oxo-1-(p-tolylsulfonyl)indoline-5-carbonitrile;

(±)-3-(2-ethoxy-5-methoxy-phenyl)-1-(4-fluorophenyl)sulfonyl-3-[2-(1-methyl-4-piperidyl)-2,6-diazaspiro[3.3]heptan-6-yl]-2-oxo-indoline-5-carbonitrile;

(+)-3-(2-ethoxy-S-methoxy-phenyl)-1-(4-fluorophenyl)sulfonyl-3-[2-(1-methyl-4-piperidyl)-2,6-diazaspiro[3.3]heptan-6-yl]-2-oxo-indoline-5-carbonitrile;

(−)-3-(2-ethoxy-5-methoxy-phenyl)-1-(4-fluorophenyl)sulfonyl-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(+)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(−)-3-(2-ethoxy-5-methoxy-phenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(±)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2-methoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-3-[2-(1-isopropyl-4-piperidyl)-2,6-diazaspiro[3.3]heptan-6-yl]-1-[(5-methoxy-2-pyridyl)sulfonyl]-2-oxo-indoline-5-carbonitrile;

(+)-3-(2-ethoxy-5-methoxy-phenyl)-3-[2-(1-isopropyl-4-piperidyl)-2,6-diazaspiro[3.3]heptan-6-yl]-1-[(5-methoxy-2-pyridyl)sulfonyl]-2-oxo-indoline-5-carbonitrile;

(−)-3-(2-ethoxy-5-methoxy-phenyl)-3-[2-(1-isopropyl-4-piperidyl)-2,6-diazaspiro[3.3]heptan-6-yl]-1-[(5-methoxy-2-pyridyl)sulfonyl]-2-oxo-indoline-5-carbonitrile;

(±)-3-(2-ethoxy-5-methoxy-phenyl)-3-[2-[1-(2-methoxyethyl)-4-piperidyl]-2,6-diazaspiro[3.3]heptan-6-yl]-1-[(5-methoxy-2-pyridyl)sulfonyl]-2-oxo-indoline-5-carbonitrile;

(+)-3-(2-ethoxy-5-methoxy-phenyl)-3-[2-[1-(2-methoxyethyl)-4-piperidyl]-2,6-diazaspiro[3.3]heptan-6-yl]-1-[(5-methoxy-2-pyridyl)sulfonyl]-2-oxo-indoline-5-carbonitrile;

(−)-3-(2-ethoxy-5-methoxy-phenyl)-3-[2-[1-(2-methoxyethyl)-4-piperidyl]-2,6-diazaspiro[3.3]heptan-6-yl]-1-[(5-methoxy-2-pyridyl)sulfonyl]-2-oxo-indoline-5-carbonitrile;

(±)-3-(2,5-dimethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2,5-dimethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2,5-dimethoxyphenyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-methoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-(2-methoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-(2-methoxy-3-pyridyl)-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-methoxyphenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile;

(+)-3-(2-methoxyphenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile;

(−)-3-(2-methoxyphenyl)-1-[(5-methoxy-2-pyridyl)sulfonyl]-3-[2-[1-(oxetan-3-yl)-4-piperidyl]-2,6-diazaspiro[3.3]heptan-6-yl]-2-oxo-indoline-5-carbonitrile;

(±)-1-(2,4-dimethoxyphenyl)sulfonyl-3-(2-ethoxy-5-methoxy-phenyl)-3-[2-(2-methyl-1-pyridyl)-2,6-diazaspiro[3.3]heptan-6-yl]-2-oxo-indoline-5-carbonitrile;

(+)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile;

(±)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile;

(+)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile;

(−)-1-(2,4-dimethoxyphenyl)sulfonyl-3-(2-ethoxy-5-methoxy-phenyl)-3-[2-(2-methyl-4-pyridyl)-2,6-diazaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-(2-methyl-4-pyridyl)-2,6-diazaspiro[3.3]heptan-6-yl]-2-oxo-indoline-5-carbonitrile;

(+)-3-(2-ethoxy-5-methoxy-phenyl)-1-[(5-methoxy-2-pyridyl)sulfonyl]-3-[2-(2-methyl-4-pyridyl)-2,6-diazaspiro[3.3]heptan-6-yl]-2-oxo-indoline-5-carbonitrile;

(−)-3-(2-ethoxy-5-methoxy-phenyl)-1-[(5-methoxy-2-pyridyl)sulfonyl]-3-[2-(2-methyl-4-pyridyl)-2,6-diazaspiro[3.3]heptan-6-yl]-2-oxo-indoline-5-carbonitrile;

(±)-3-(2-methoxyphenyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(+)-3-(2-methoxyphenyl)-1[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(−)-3-(2-methoxyphenyl)-1-[(5-methoxy-2-pyridyl)sulfonyl]-3-[2-(4-methylpiperazin-1-yl)-6-azaspiro[3.3]heptan-6-yl]-2-oxo-indolin-5-carbonitrile;

(±)-3-(2-ethoxy-3-pyridyl)-1-[(5-methoxy-2-pyridyl)sulfonyl]-3-[2-(4-methylpiperazin-1-yl)-6-azaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-[4-(oxetan-3-yl)piperazin-1-yl]-6-azaspiro[3.3]heptan-6-yl]-2-oxo-indoline-5-carbonitrile;

(+)-3-(2-ethoxy-5-methoxy-phenyl)-1-[(5-methoxy-2-pyridyl)sulfonyl]-3-[2-[4-(oxetan-3-yl)piperazin-1-yl]-6-azaspiro[3.3]heptan-6-yl]-2-oxo-indoline-5-carbonitrile;

(−)-3-(2-ethoxy-5-methoxy-phenyl)-1-[(5-methoxy-2-pyridyl)sulfonyl]-3-[2-[4-(oxetan-3-yl)piperazin-1-yl]-6-azaspiro[3.3]heptan-6-yl]-2-oxo-indoline-5-carbonitrile;

(±)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-6-carbonitrile;

(+)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-6-carbonitrile;

(−)-3-(2-ethoxy-5-methoxy-phenyl)-1-[(5-methoxy-2-pyridyl)sulfonyl]-3-[2-(1-methyl-4-piperidyl)-2,6-diazaspiro[3.3]heptan-6-yl]-2-oxo-indoline-6-carbonitrile;

(±)-3-[2-(1,1-difluoroethyl)-3-pyridyl]-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(+)-3-[2-(1,1-difluoroethyl)-3-pyridyl]-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(−)-3-[2-(1,1-difluoroethyl)-3-pyridyl]-1-[(5-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-[(6-methoxy-3-pyridyl)sulfonyl]-3-[2-(1-methyl-4-piperidyl)-2,6-diazaspiro[3.3]heptan-6-yl]-2-oxo-indoline-5-carbonitrile;

(3S)-3-(2-ethoxy-5-methoxy-phenyl)-1-[(6-methoxy-3-pyridyl)sulfonyl]-3-[2-(1-methyl-4-piperidyl)-2,6-diazaspiro[3.3]heptan-6-yl]-2-oxo-indoline-5-carbonitrile;

(3R)-3-(2-ethoxy-5-methoxy-phenyl)-1-[(6-methoxy-3-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-1-[(6-methoxy-2-pyridyl)sulfonyl]-3-[2-(1-methyl-4-piperidyl)-2,6-diazaspiro[3.3]heptan-6-yl]-2-oxo-indoline-5-carbonitrile;

(3S)-3-(2-ethoxy-5-methoxy-phenyl)-1-[(6-methoxy-2-pyridyl)sulfonyl]-3-[2-(1-methyl-4-piperidyl)-2,6-diazaspiro[3.3]heptan-6-yl]-2-oxo-indoline-5-carbonitrile;

(3R)-3-(2-ethoxy-5-methoxy-phenyl)-1-[(6-methoxy-2-pyridyl)sulfonyl]-3-[2-(1-methyl-4-piperidyl)-2,6-diazaspiro[3.3]heptan-6-yl]-2-oxo-indoline-5-carbonitrile;

(±)-3-(2-ethoxy-5-methoxy-phenyl)-3-[2-(1-methyl-4-piperidyl)-2,6-diazaspiro[3.3]heptan-6-yl]-2-oxo-1-(2-pyridylsulfonyl)indoline-5-carbonitrile;

(3S)-3-(2-ethoxy-5-methoxy-phenyl)-3-[2-(1-methyl-4-piperidyl)-2,6-diazaspiro[3.3]heptan-6-yl]-2-oxo-1-(2-pyridylsulfonyl)indoline-5-carbonitrile;

(3R)-3-(2-ethoxy-5-methoxy-phenyl)-3-[2-(1-methyl-4-piperidyl)-2,6-diazaspiro[3.3]heptan-6-yl]-2-oxo-1-(2-pyridylsulfonyl)indoline-5-carbonitrile;

(±)-1-[(5-chloro-2-pyridyl)sulfonyl]-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

(3S)-1-[(5-chloro-2-pyridyl)sulfonyl]-3-(2-ethoxy-5-methoxy-phenyl)-3-[2-(1-methyl-4-piperidyl)-2,6-diazaspiro[3.3]heptan-6-yl]-2-oxo-indoline-5-carbonitrile; and (3R)-1-[(5-chloro-2-pyridyl)sulfonyl]-3-(2-ethoxy-5-methoxy-phenyl)-3-[2-(1-methyl-4-piperidyl)-2,6-diazaspiro[3.3]heptan-6-yl]-2-oxo-indoline-5-carbonitrile;

or a pharmaceutically acceptable salt thereof.

29. A pharmaceutical composition comprising at least one compound of the formula I as defined in claim 1 and/or an N-oxide, a stereoisomer or at least one pharmaceutically acceptable salt thereof and at least one pharmaceutically acceptable carrier.

30. A method for treating a vasopressin related disease selected from the group consisting of depressive disorders, an anxiety disorder or stress-dependent anxiety disorder, and substance-related additive disorders, comprising administering to a patient in need thereof an effective amount of at least one compound of the formula I as defined in claim 1 or at least one N-oxide, stereoisomer or pharmaceutically acceptable salt thereof.

31. A method for treating a vasopressin related disease selected from the group consisting of depressive disorders, an anxiety disorder or stress-dependent anxiety disorder, and substance-related additive disorders, comprising administering to a patient in need thereof an effective amount of a pharmaceutical composition as defined in claim 29.

\* \* \* \* \*